US009563744B1

(12) United States Patent
Röder et al.

(10) Patent No.: US 9,563,744 B1
(45) Date of Patent: Feb. 7, 2017

(54) METHOD OF PREDICTING DEVELOPMENT AND SEVERITY OF GRAFT-VERSUS-HOST DISEASE

(71) Applicant: Biodesix, Inc., Boulder, CO (US)

(72) Inventors: Heinrich Röder, Steamboat Springs, CO (US); Joanna Röder, Steamboat Springs, CO (US)

(73) Assignee: Biodesix, Inc., Boulder, CO (US)

( * ) Notice: Subject to any disclaimer, the term of this patent is extended or adjusted under 35 U.S.C. 154(b) by 0 days.

(21) Appl. No.: 14/949,229

(22) Filed: Nov. 23, 2015

Related U.S. Application Data

(60) Provisional application No. 62/086,806, filed on Dec. 3, 2014.

(51) Int. Cl.
| | |
|---|---|
| *H01J 49/26* | (2006.01) |
| *H01J 49/00* | (2006.01) |
| *A61K 39/395* | (2006.01) |
| *A61K 38/17* | (2006.01) |
| *G06F 19/00* | (2011.01) |
| *G01N 33/49* | (2006.01) |
| *H01J 49/16* | (2006.01) |
| *H01J 49/40* | (2006.01) |

(52) U.S. Cl.
CPC ......... *G06F 19/3431* (2013.01); *G01N 33/492* (2013.01); *H01J 49/164* (2013.01); *H01J 49/40* (2013.01)

(58) Field of Classification Search
USPC .. 250/281, 282, 425, 492.1, 526; 424/130.1, 142.1; 435/4, 6.1, 7.1, 7.25, 30, 435/39, 290.2, 317.1; 536/24.3; 702/19
See application file for complete search history.

(56) References Cited

U.S. PATENT DOCUMENTS

| | | | |
|---|---|---|---|
| 7,763,425 B2 * | 7/2010 | Perreault .............. | C12Q 1/6881 435/6.12 |
| 8,153,130 B2 | 4/2012 | Shibuya et al. | |
| 8,603,754 B2 | 12/2013 | Shibuya et al. | |
| 8,637,232 B2 | 1/2014 | Lama | |
| 9,211,314 B2 * | 12/2015 | Roder .................. | A61K 38/179 |
| 2015/0283206 A1 * | 10/2015 | Roder .................. | A61K 38/179 514/9.6 |

(Continued)

OTHER PUBLICATIONS

S. Paczesny, Discovery and validation of graft-versus-host disease biomarkers, Blood vol. 121 No. 4 pp. 585-594 (2013).

(Continued)

*Primary Examiner* — Bernard Souw
(74) *Attorney, Agent, or Firm* — McDonnell Boehnen Hulbert & Berghoff LLP

(57) ABSTRACT

A classifier and method for predicting or characterizing graft-versus-host disease in a patient after receiving a transplant of pluripotent hematopoietic stem cells or bone marrow. The classifier operates on mass-spectral data obtained from a blood-based sample of the patient and is configured as a combination of filtered mini-classifiers using a regularized combination method, such as logistic regression with extreme drop-out. The method also uses a "deep-MALDI" mass spectrometry technique in which the blood-based samples are subject to at least 100,000 laser shots in MALDI-TOF mass spectrometry in order to reveal greater spectral content and detect low abundance proteins circulating in serum associated with graft-versus-host disease.

11 Claims, 15 Drawing Sheets

(56) References Cited

U.S. PATENT DOCUMENTS

2016/0163522 A1* 6/2016 Roder ............... H01J 49/0036
250/282

OTHER PUBLICATIONS

M.T. Vander Lugt et al., ST2 as a Marker for Risk of Therapy-Resistant Graft-versus-Host Disease and Death, NEJM vol. 369 No. 6 pp. 529-539 (2013).

E. Weissinger et al., Proteomic patterns predict acute graft-versus-host disease after allogeneic hematopoietic stem cell transplantation, Blood vol. 109 No. 12 pp. 5511-5519 (2007).

G. Socié, Graft-versus-host disease: proteomics comes of age, Blood vol. 113 No. 2 p. 271-272 (2009).

S. Paczesny et al., Blood vol. 113 No. 2 pp. 273-278 (2009).

Y-B Chen et al., Biomarkers for acute GVHD: can we predict the unpredictable? Bone Marrow Transplantation vol. 48 pp. 755-760 (2013).

R. Srinivasan et al., Accurate diagnosis of acute graft-versus-host disease using serum proteomic pattern analysis, Experimental Hematology vol. 34 pp. 796-801 (2006).

S. Paczesny et al., Graft-versus-Host Disease Biomarkers: Omics and Personalized Medicine, Int. J. Hematol. vol. 98 No. 3 pp. 275-292 (2013).

J. Levine et al., Clinical applications for biomarkers of acute and chronic graft-versus-host disease, Biol. Blood Marrow Transplan. vol. 18 (1 Suppl): S116-S124 (2012).

M. Cuzzola et al., A molecular and computational diagnostic approach identifies FOXP3, ICOS, CD52 and CASP1 as the most informative biomarkers in acute graft-versus-host disease, Haematologica vol. 97 No. 10 pp. 1532-1538 (2012).

J. Rozmus et al., Biomarkers in Chronic Graft-versus-Host Disease, Expert Rev. Hematol. vol. 4 No. 3 pp. 329-342 (2011).

J. Levine et al., Acute graft-versus-host disease biomarkers measured during therapy can predict treatment outcomes: a Blood and Marrow Transplant Clinical Trials Network study. Blood, vol. 119 No. 16 pp. 3854-3860 (2012).

Yu et al., "Biomarker panel for Chronic Graft-Versus-Host Disease", Journal of Clinical Oncology, p. 1-10 (2016).

* cited by examiner

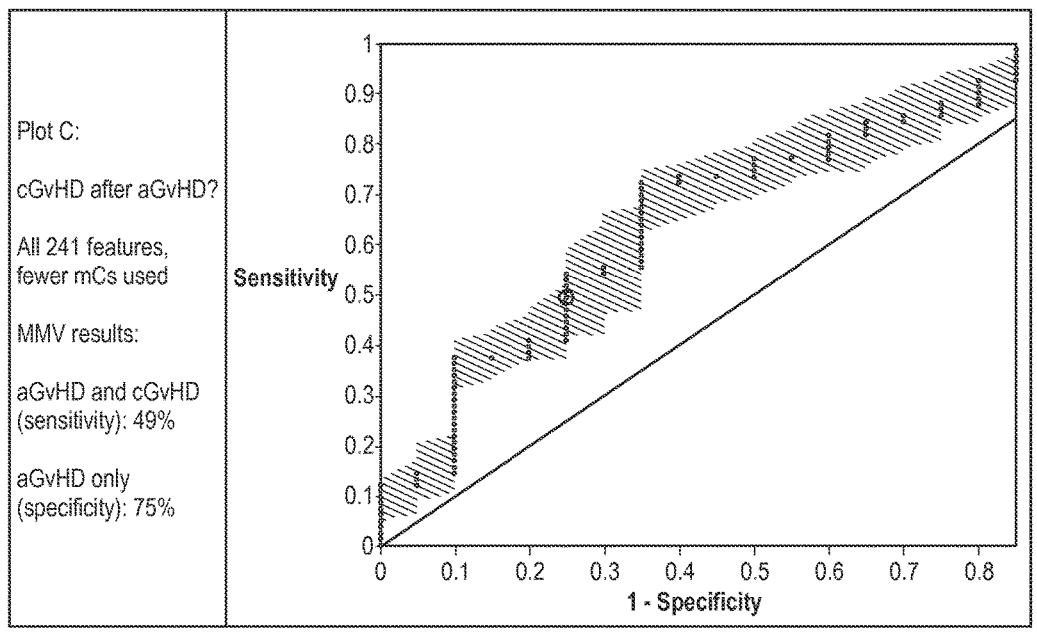
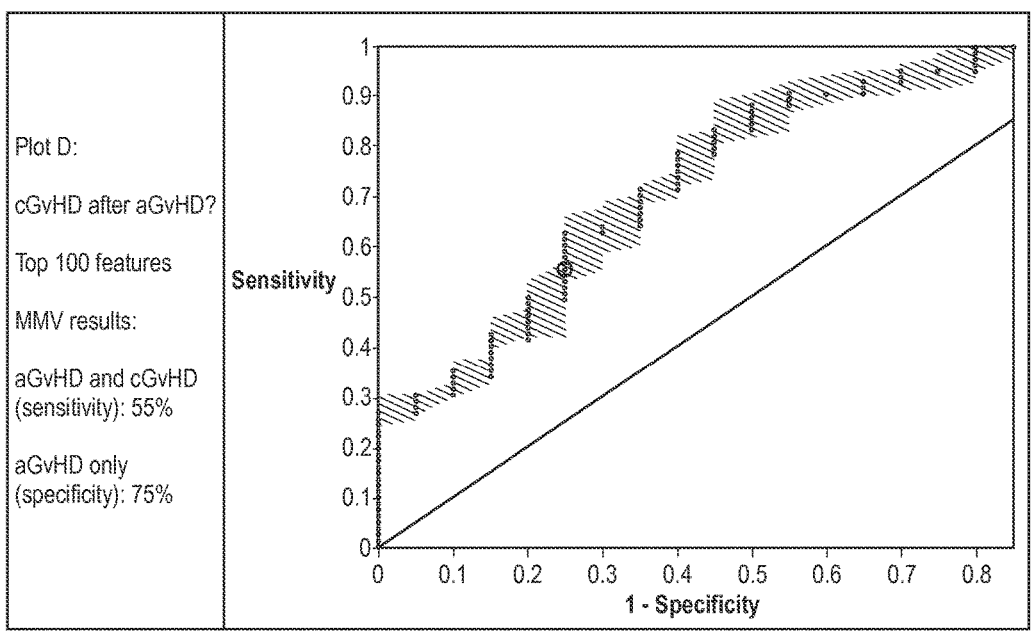

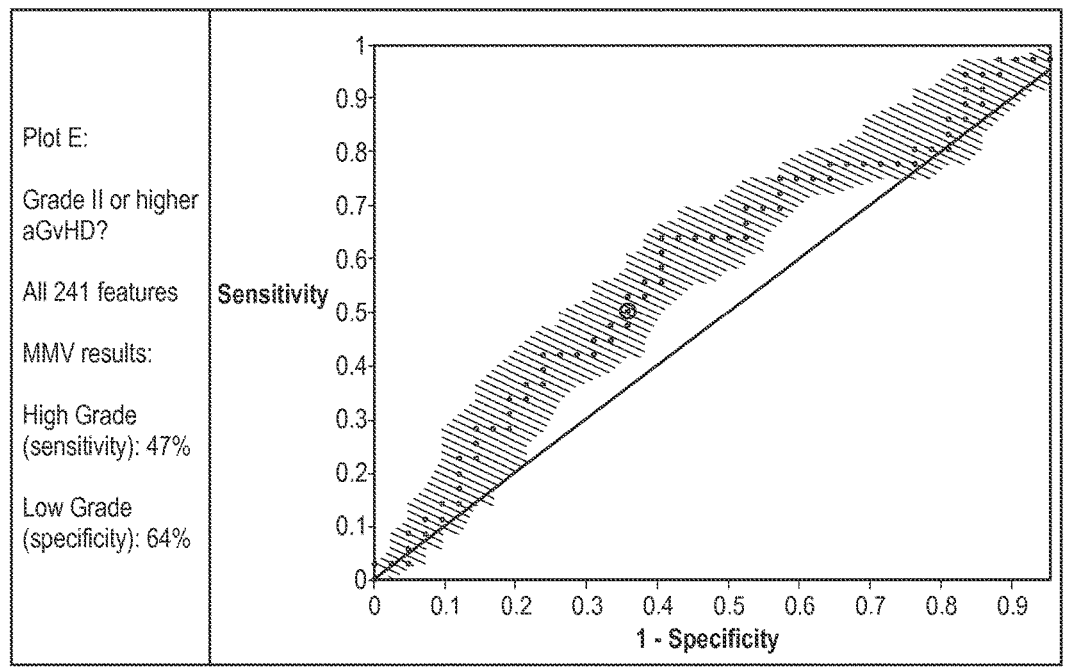
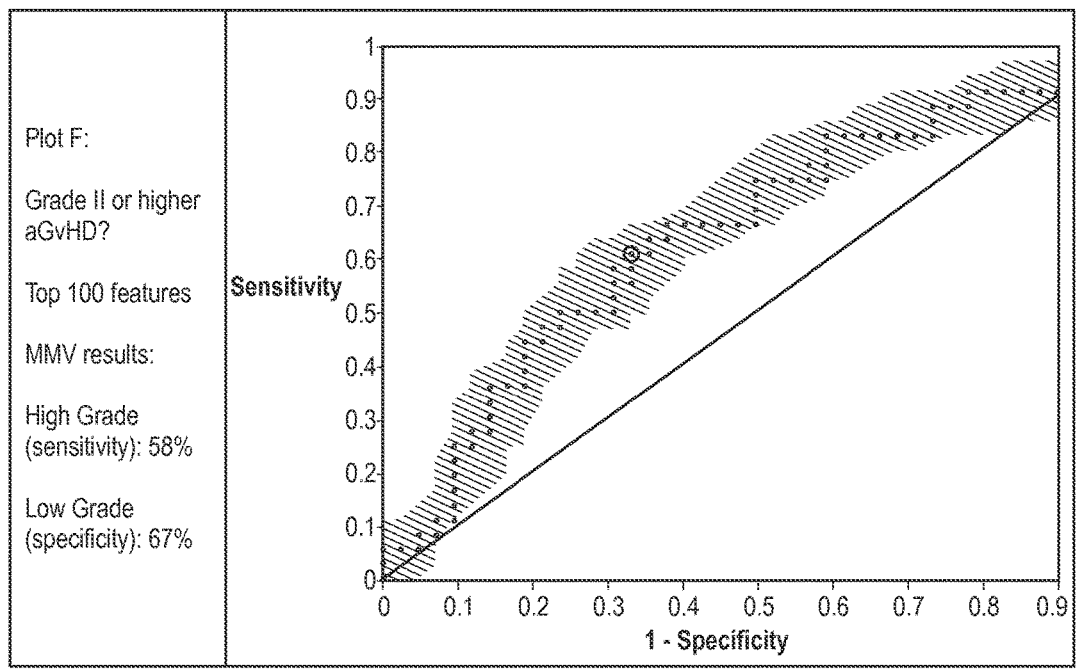

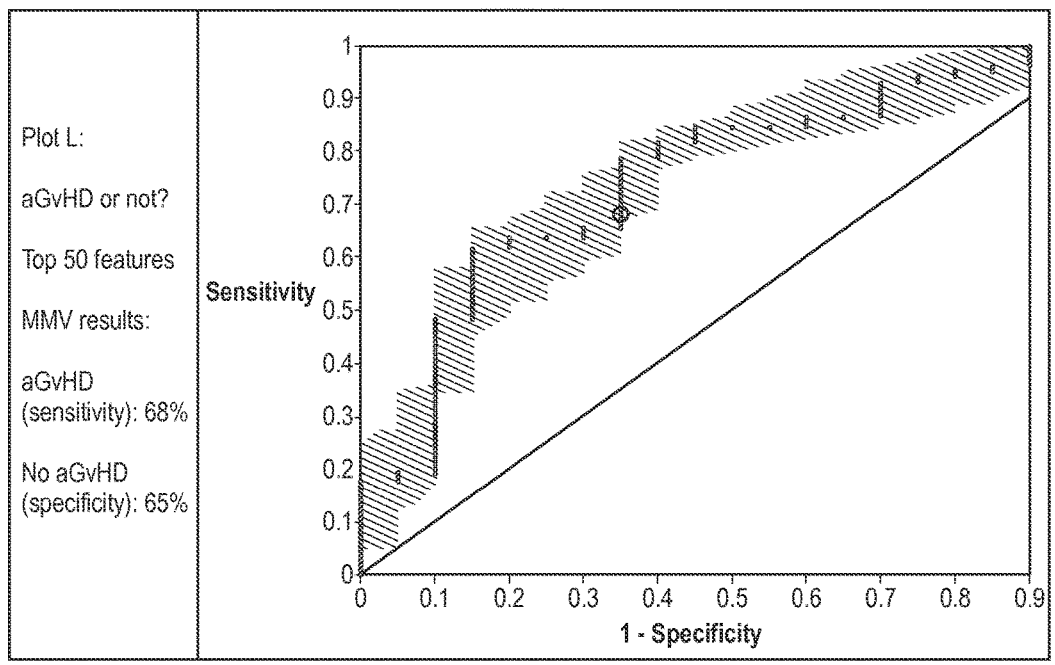

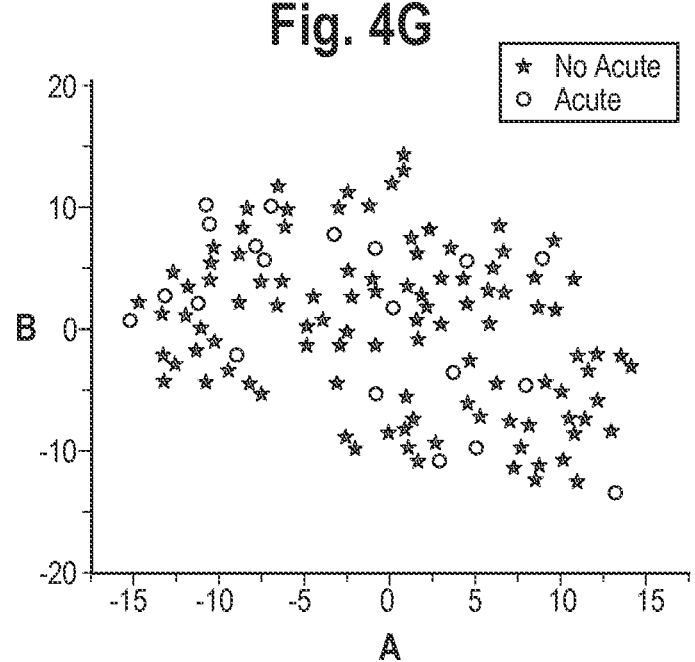
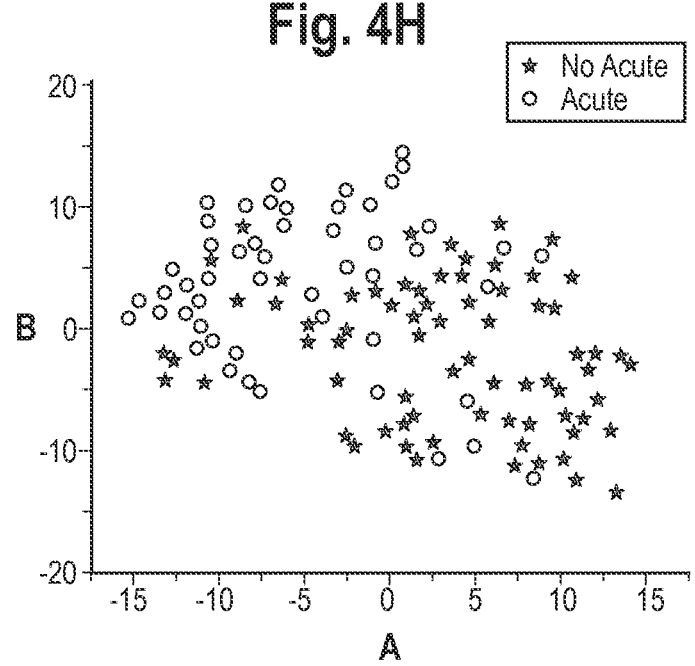

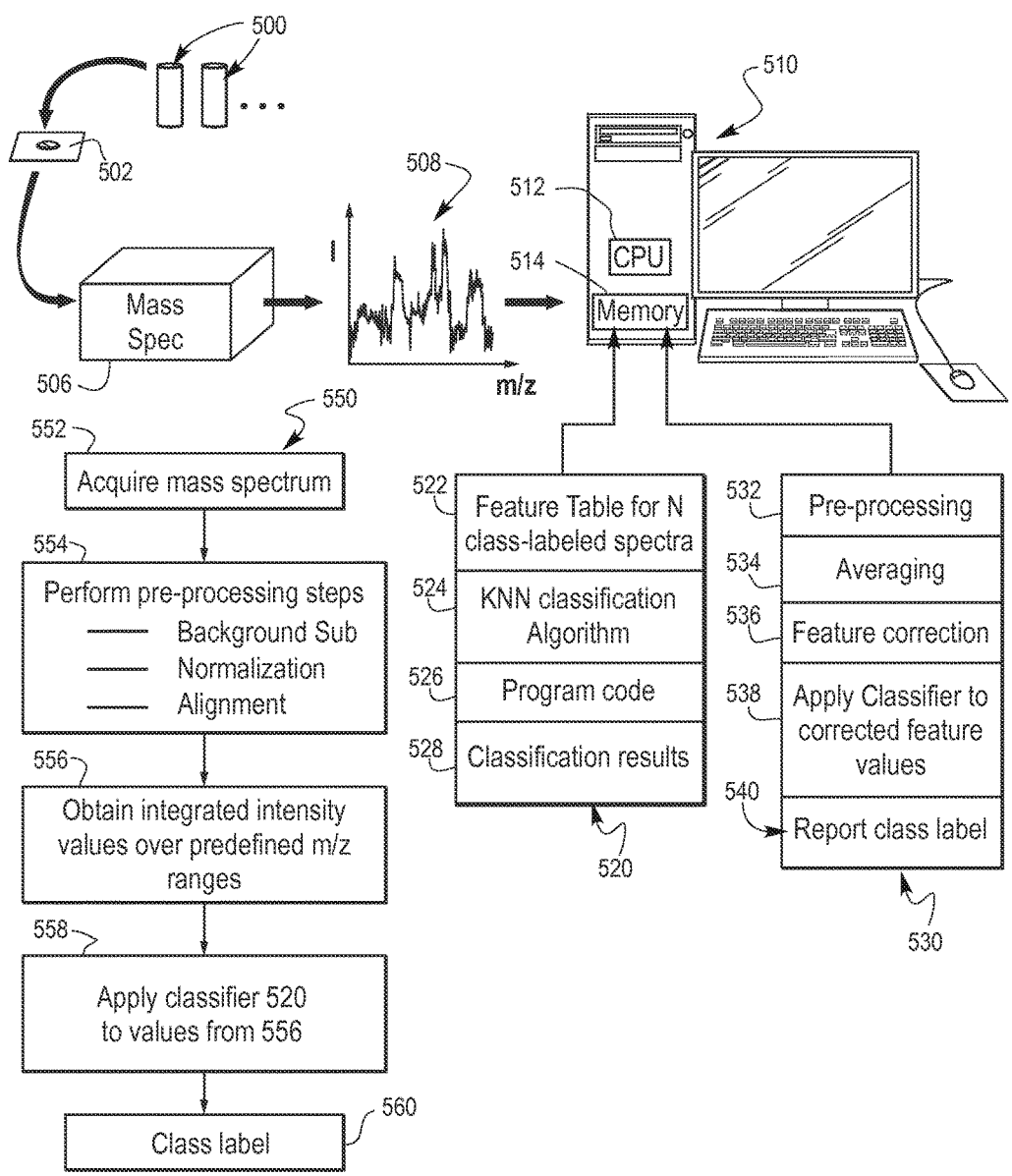

METHOD OF PREDICTING DEVELOPMENT AND SEVERITY OF GRAFT-VERSUS-HOST DISEASE

PRIORITY

This application claims priority benefits under 35 U.S.C. §119 to U.S. provisional application Ser. No. 62/086,806 filed Dec. 3, 2014, the contents of which are incorporated by reference herein.

BACKGROUND

Transplants of pluripotent hematopoietic stem cells (PHSC) or bone marrow are an effective immunotherapy against hematological malignancies. However, graft-versus-host disease (GvHD) remains a major source of morbidity and mortality following transplant. GvHD is a systemic immunological disorder that develops when donor immune cells attack not just residual tumor cells, but also normal host tissue, particularly the skin, liver, and gastro-intestinal tract. GvHD is traditionally divided into two groups: acute (aGvHD), which arises before the 100 day mark post-transplant, and chronic (cGvHD), which occurs after 100 days post-transplant; however, the current consensus is that clinical manifestations and not time after transplantation determine whether the clinical syndrome is considered aGvHD or cGvHD. While mild aGvHD (grade I or II) is associated with little morbidity and almost no mortality, higher grades (III and IV) are associated with very high mortality rates.

Currently available diagnostic and staging tools frequently fail to identify those at higher risk of GvHD development, morbidity, treatment unresponsiveness and death. A number of candidate aGvHD biomarkers are currently under active investigation as promising diagnostic and prognostic tools, but to the inventors' knowledge none have yet been validated in multicenter prospective trials. Prior art describing such biomarkers includes U.S. Pat. No. 8,637,232 (disclosing biomarkers predicting, among other things, GvHD in lung transplant patients); U.S. Pat. Nos. 8,603,754; 8,153, 130; and 7,763,425. The prior art also includes following articles: S. Paczesny, *Discovery and validation of graft-versus-host disease biomarkers*, Blood vol. 121 no. 4 pp. 585-594 (2013); M. T. Vander Lugt et al., *ST2 as a Marker for Risk of Therapy-Resistant Graft-versus-Host Disease and Death*, NEJM vol. 369 no. 6 pp. 529-539 (2013); E. Weissinger et al., *Proteomic patterns predict acute graft-versus-host disease after allogeneic hematopoietic stem cell transplantation*, Blood vol. 109 no. 12 pp. 5511-5519 (2007); G. Socié, *Graft-versus-host disease: proteomics comes of age*, Blood vol. 113 no. 2 p. 271-272 (2009); S. Paczesny et al., Blood vol. 113 no. 2 pp. 273-278 (2009); Y-B Chen et al., *Biomarkers for acute GVHD: can we predict the unpredictable?* Bone Marrow Transplantation vol. 48 pp. 755-760 (2013); R. Srinivasan et al., *Accurate diagnosis of acute graft-versus-host disease using serum proteomic pattern analysis*, Experimental Hematology vol. 34 pp. 796-801 (2006); S. Paczesny et al., *Graft-versus-Host Disease Biomarkers: Omics and Personalized Medicine*, Int. J. Hematol. vol. 98 no. 3 pp. 275-292 (2013). J. Levine et al., *Clinical applications for biomarkers of acute and chronic graft-versus-host disease*, Biol. Blood Marrow Transplan. vol. 18 (1 Suppl): S116-S124 (2012); M. Cuzzola et al., *A molecular and computational diagnostic approach identifies FOXP3, ICOS, CD52 and CASP1 as the most informative biomarkers in acute graft-versus-host disease*, Haematologica vol. 97 no. 10 pp. 1532-1538 (2012), J. Rozmus et al., *Biomarkers in Chronic Graft-versus-Host Disease*, Expert Rev. Hematol. vol. 4 no. 3 pp. 329-342 (2011); J. Levine et al., *Acute graft-versus-host disease biomarkers measured during therapy can predict treatment outcomes: a Blood and Marrow Transplant Clinical Trials Network study*. Blood, vol. 119 no. 16 pp. 3854-3860 (2012). The Srinivasan et al. paper describes SELDI-TOF-based proteomic analysis as a rapid and accurate method to diagnose aGvHD and is considered the closest known prior art.

Clinical tests predictive of the development of aGvHD and cGvHD (either de novo or secondary to aGvHD), as well as tests predicting the severity of the disease (both acute and chronic) would be of great interest, because they could guide therapeutic decisions towards more or less aggressive treatment. The present invention meets that need.

SUMMARY

In a first aspect, a method for assessing the risk of a patient receiving a transplant of pluripotent hematopoietic stem cells (PHSC) or bone marrow developing graft-versus-host disease or characterizing the disease is disclosed. The method includes the steps of performing MALDI-TOF mass spectrometry on a blood-based sample obtained from the patient after the PHSC or bone marrow transplant by subjecting the sample to at least 100,000 laser shots and acquiring mass spectral data. The data takes the form of integrated intensity values of a multitude of pre-determined mass-spectral features (m/z ranges). This step preferably makes use of the so-called "deep MALDI" mass spectrometry technique described in U.S. Patent application of H. Röder et al., Ser. No. 13/836,436 filed Mar. 15, 2013, US patent application publication no. 2013/0320203 the contents of which are incorporated by reference herein. The deep MALDI methodology (using at least 100,000 laser shots) results in the obtaining of much more spectral information, including spectral information of low abundance intact proteins circulating in serum or plasma, than is typically revealed from standard "dilute and shoot" ~2,000 laser shot spectra.

The method continues with a step of operating on the mass spectral data with a programmed computer implementing a classifier configured as a combination of filtered mini-classifiers using a regularized combination method. This step includes the use of what we have termed "CMC/D" classifiers (Combination of Mini-Classifiers with Dropout regularization), as described in pending U.S. patent application of H. Röder et al., Ser. No. 14/486,442 filed Sep. 15, 2014, U.S. patent application publication no. 2015/0102216, the content of which is incorporated by reference herein. The method of generating a CMC/D classifier and using it to generate a class label to predict or characterize graft-versus-host disease is described in detail below.

In the operating step the classifier compares the integrated intensity values with feature values of a reference set of class-labeled mass spectral data obtained from a multitude of patients having received a transplant of PHSC or bone marrow and generates a class label for the sample using a classification algorithm, such as k-nearest neighbors. The class label is associated with the risk of a patient providing the sample developing graft-versus-host disease or characterizing the graft-versus-host disease, e.g., staging the disease or predicting whether chronic graft-versus-host disease will follow acute graft-versus-host disease. The reference set of class-labeled mass spectral data may take the form of a training set used to develop the classifier, or may take the form of some subset of the training set.

In one embodiment, the final class label that is reported may take the form of a panel of class labels associated with the sample, each class label associated with a different clinical question in regards to graft-versus-host disease. In this embodiment, the operating step is performed multiple times by different classifiers, each configured as a combination of filtered mini-classifiers using a regularized combination method and addressing a different clinical question associated with the development or characterization of graft-versus-host disease. The method then generates a panel (or set) of class label results, one for each operating step/clinical question.

In one possible embodiment, one of the classifiers addresses the clinical question of whether the patient is likely to develop aGvHD. In another embodiment, one of the classifiers addresses the clinical question of whether the patient is likely to develop aGvHD at grade II or higher as compared to not developing aGvHD or developing aGvHD only at grade 1. In another embodiment, one of the classifiers addresses the clinical question of whether the patient is likely to develop cGvHD after developing aGvHD.

We also describe the mass spectrometry features (m/z ranges) which are used for classification. See Appendix A. The use of deep MALDI mass spectrometry reveals hundreds of potential features for classification (i.e., features at which integrated intensity values are obtained from the spectrum under test and features for which integrated intensity values are stored from the reference set). In one embodiment, the integrated intensity values are obtained from at least 50 features listed in Appendix A, such as 50 features, 100 features or 200 or more features.

In another aspect, a classifier is disclosed for assessing the risk of a patient receiving a transplant of PHSC or bone marrow developing GvHD or characterizing such disease. The classifier includes a memory storing a reference set of mass spectral data obtained from a multitude of patients having received a transplant of PHSC or bone marrow and associated class label, and a programmed computer configured to implement a classifier configured as a combination of filtered mini-classifiers with drop-out regularization. The reference set of mass spectral data includes feature values of at least 50 m/z features listed in Appendix A.

In still another aspect, a laboratory testing system is described for conducting tests on blood-based samples from patients receiving PHSC or bone marrow transplants and assessing risk of the patients developing graft-versus-host disease or characterizing such disease. The laboratory test center includes a MALDI-TOF mass spectrometer configured to conduct mass spectrometry on a blood-based sample from a patient by subjecting the sample to at least 100,000 laser shots and acquiring resulting mass spectral data. The laboratory test center also includes a memory storing a reference set of mass spectral data obtained from a multitude of patients having received a transplant of PHSC or bone marrow and an associated class label. The laboratory test center also includes a programmed computer configured to implement a classifier configured as a combination of filtered mini-classifiers with drop-out regularization. The reference set of mass spectral data includes feature values of at least 50 m/z features listed in Appendix A. The computer is programmed to generate a class label for the sample, wherein the class label is associated with the risk of a patient providing the sample developing GvHD or characterizing such disease.

BRIEF DESCRIPTION OF THE DRAWINGS

FIGS. 2A-2L are plots of Receiver Operating Curves (ROC) corresponding to the classifier performances summarized in Table 8 for different clinical questions related to predicting or characterizing GvHD. The open circle indicates the position of a 0.5 average probability cutoff. The shaded band indicates the 90% confidence interval on the curve as estimated by bootstrap over master classifiers MCs where a sample is in the test set for each sample. NB: there is no plot "2I", consistent with Table 8.

FIGS. 4A-4I are t-Stochastic Neighbor Embedding (t-SNE) plots for class labels used for classifier development (left hand side) and the resulting classifications (right hand side) for (FIG. 4A) and (FIG. 4B) occurrence of cGvHD or not post aGvHD (study #2), (FIG. 4C) and (FIG. 4D) grade of aGvHD (study #4), (FIG. 4E) and (FIG. 4F) severity of cGvHD (study #7), (FIG. 4G) and (FIG. 4H) occurrence of aGvHD (study #9). FIG. 4I shows the classifications obtained from the semi-unsupervised learning approach applied to study #5. In the plots, A and B are the two coordinates of the t-SNE low dimensional space.

FIG. 5 is a diagram showing a laboratory test processing center including a mass spectrometer, computer configured as a classifier and memory storing a reference set of class-labeled mass spectral data used for performing tests on blood samples obtained from patients receiving PHSC or bone marrow transplants to predict risk of GvHD or characterizing such disease.

DETAILED DESCRIPTION

Figure 1:
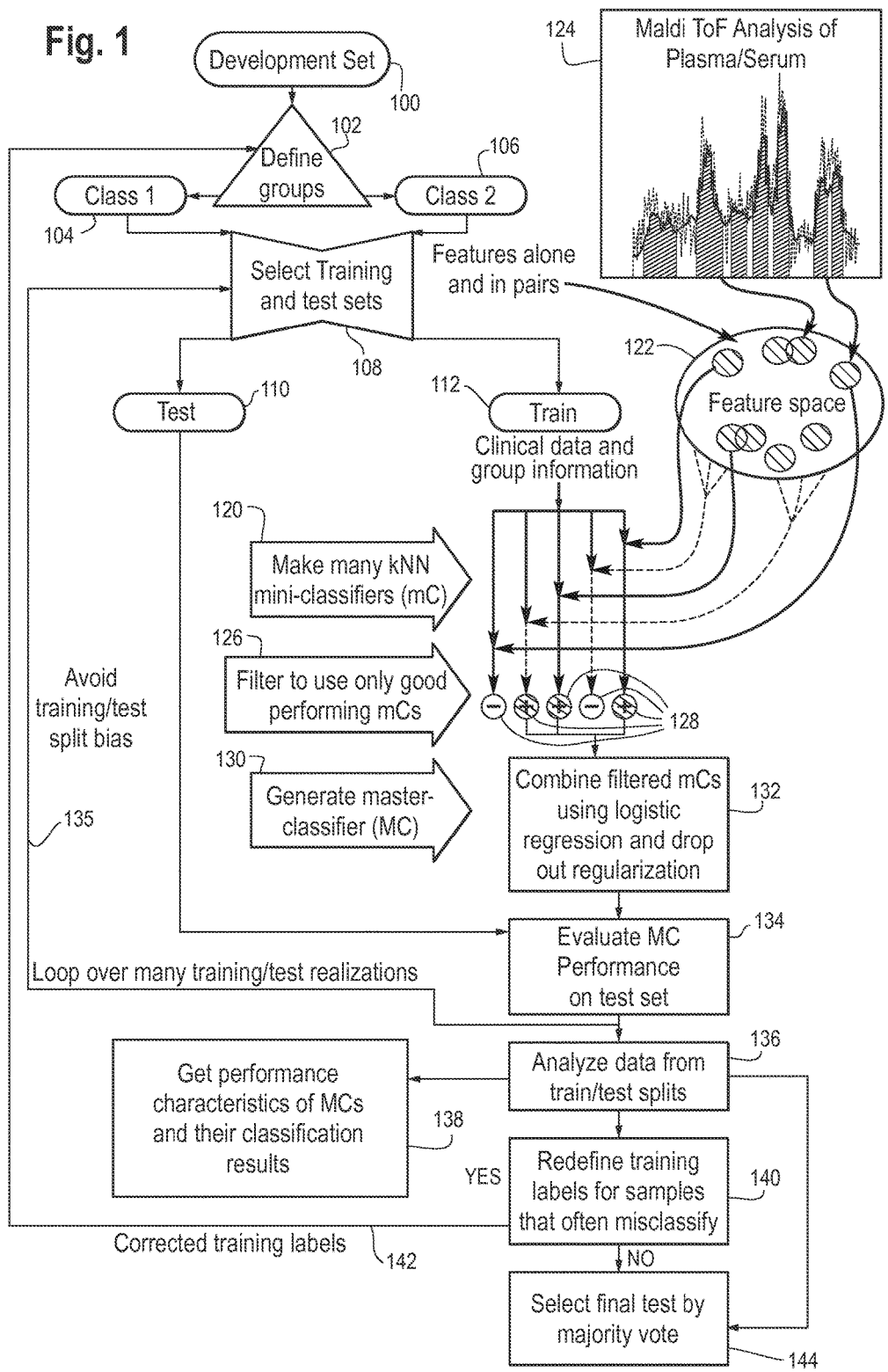
FIG. 1 is a flow-chart showing a classifier development methodology we used to create the GvHD classifiers disclosed in this document. The methodology uses mass-spectral data associated with blood-based samples obtained from patients after receiving PHSC or bone marrow transplants.
Figure 2A:
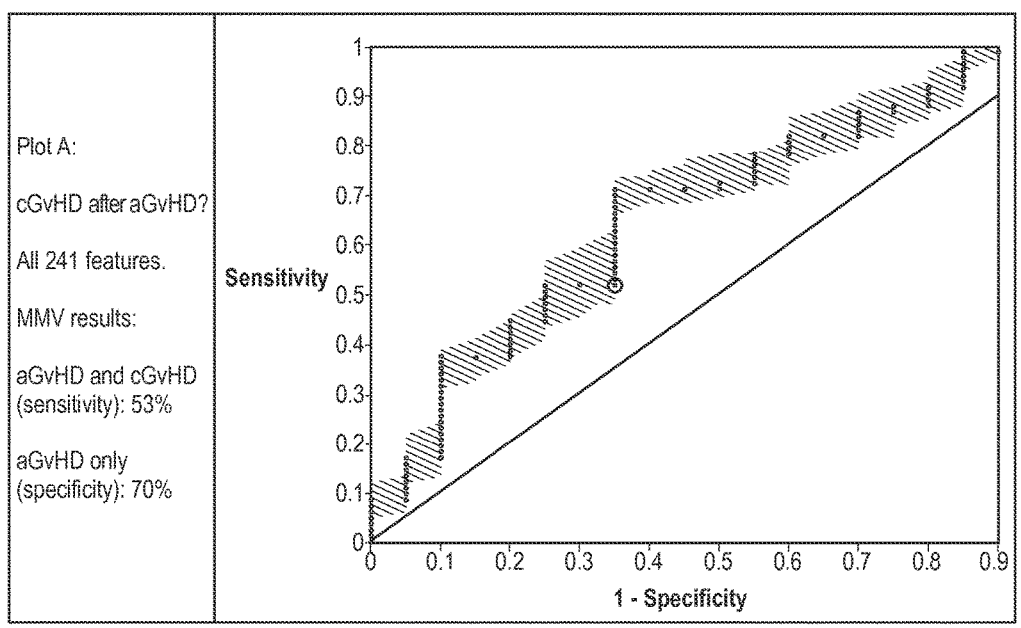
Figure 2B:
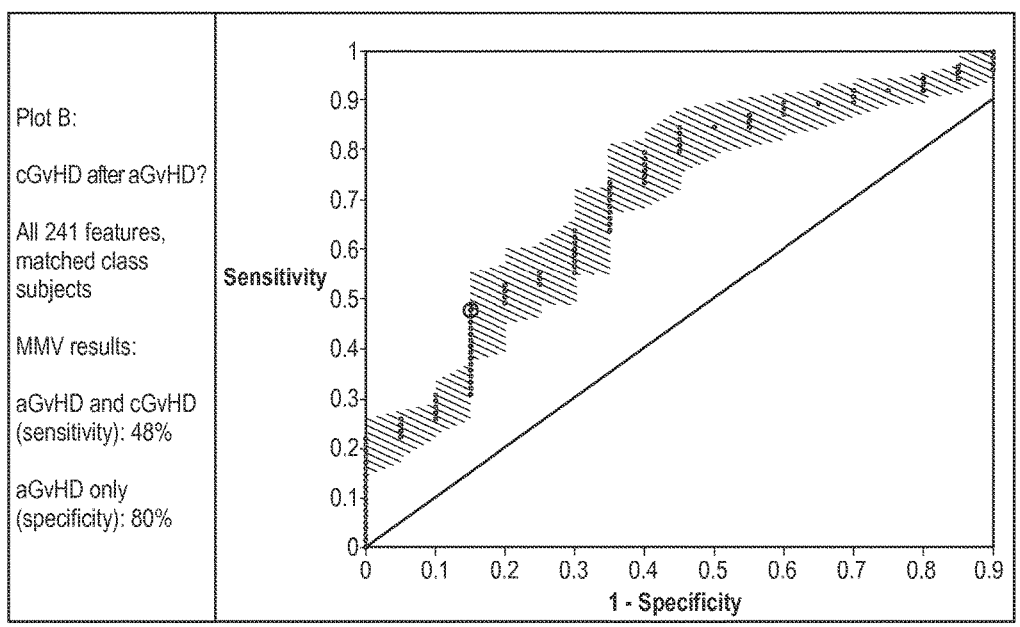
Figure 2G:
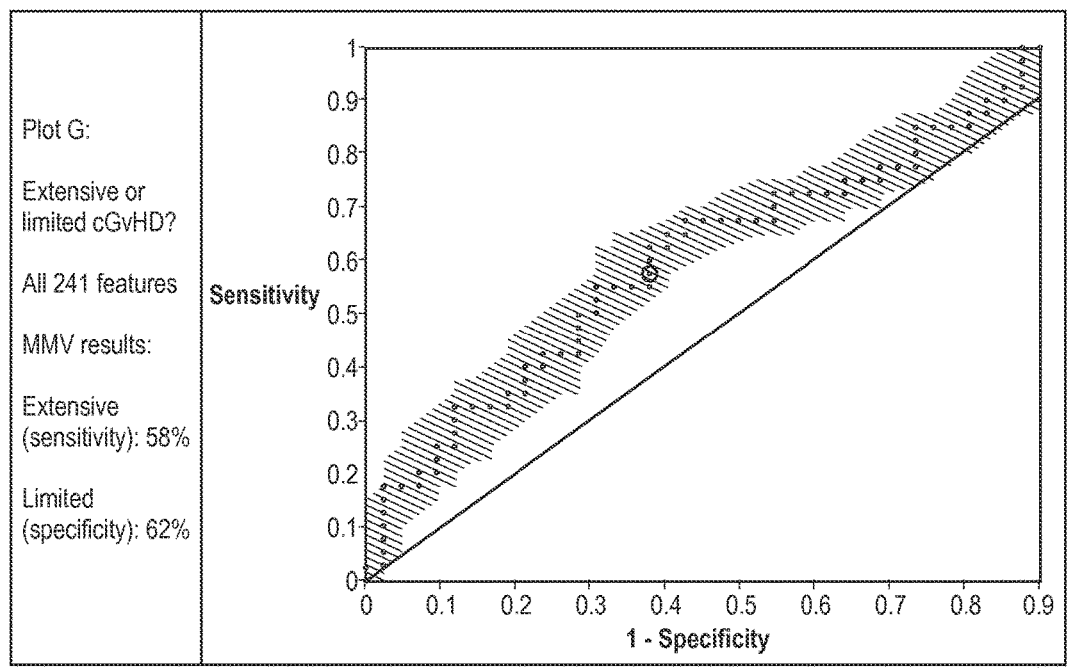
Figure 2H:
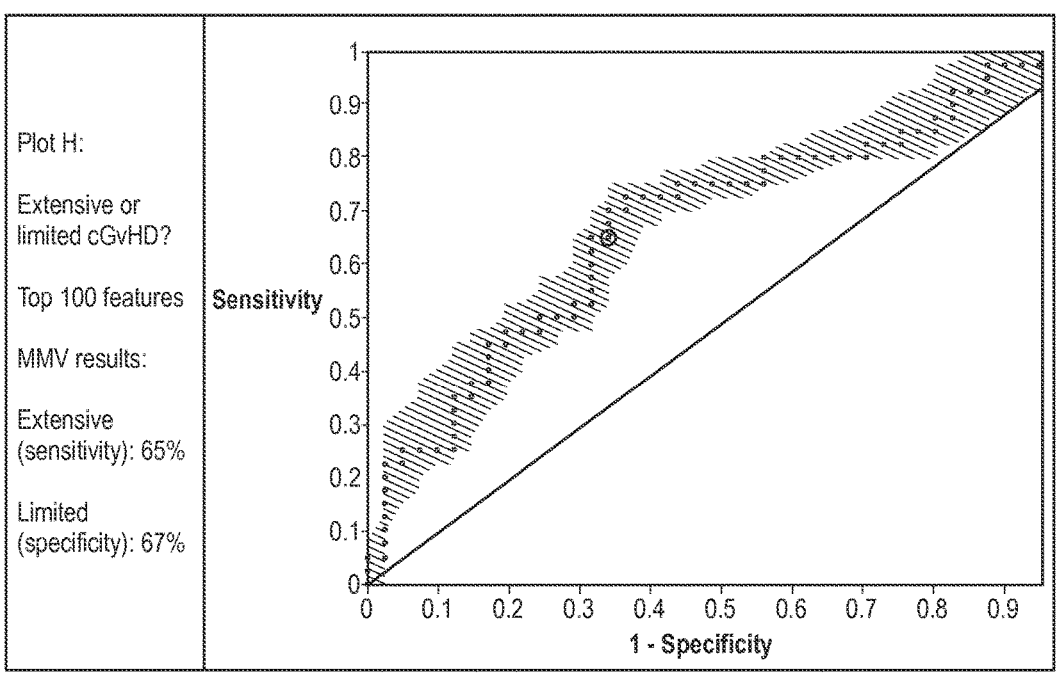
Figure 2J:
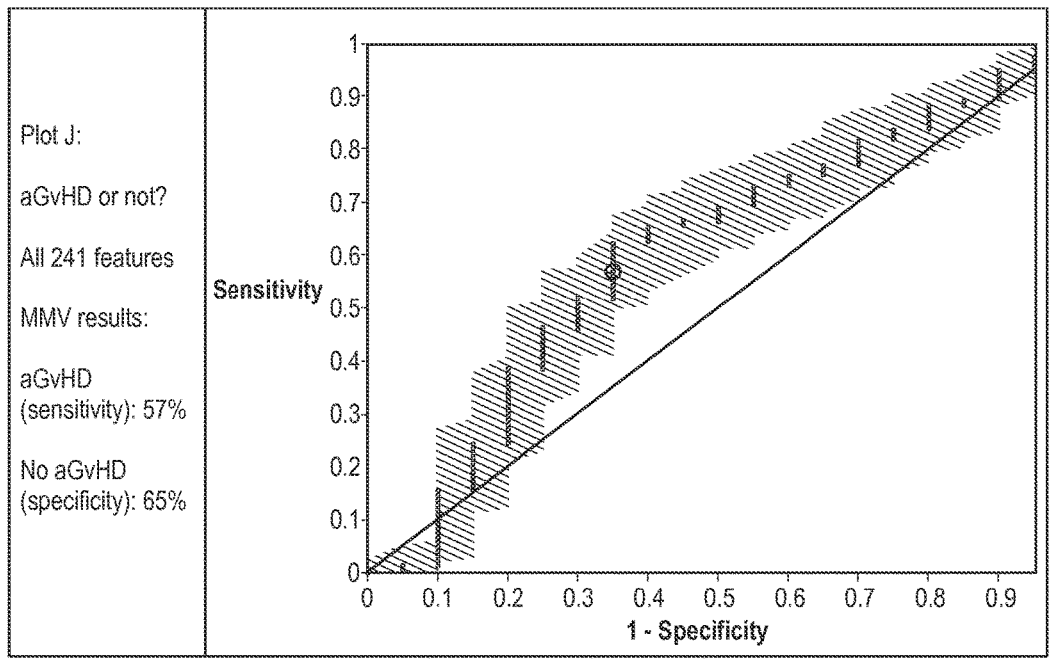
Figure 2K:
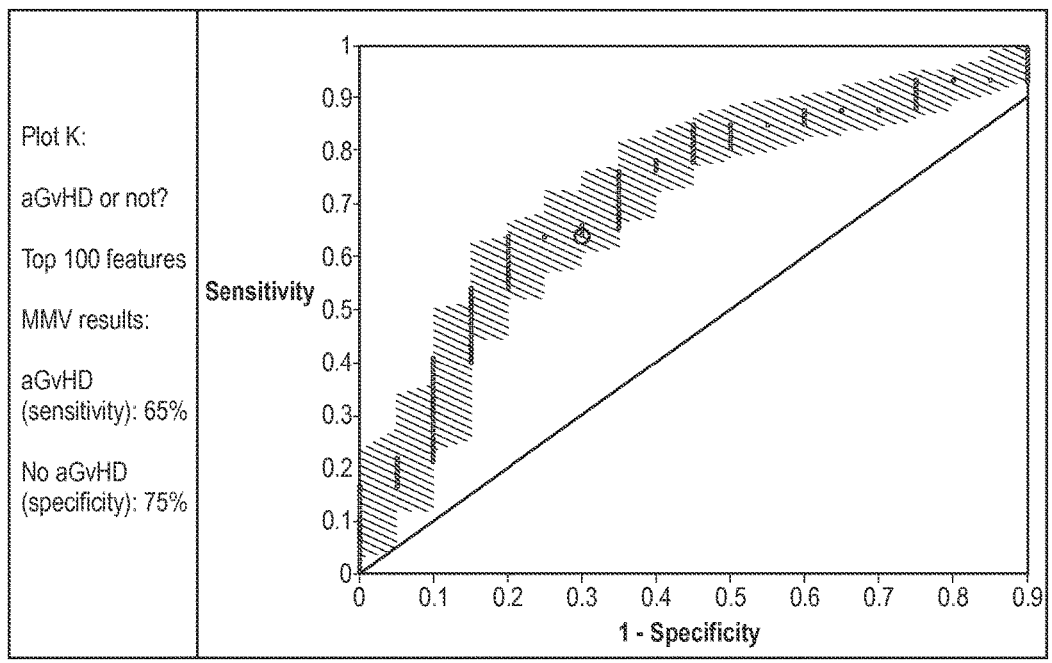
Figure 3A:
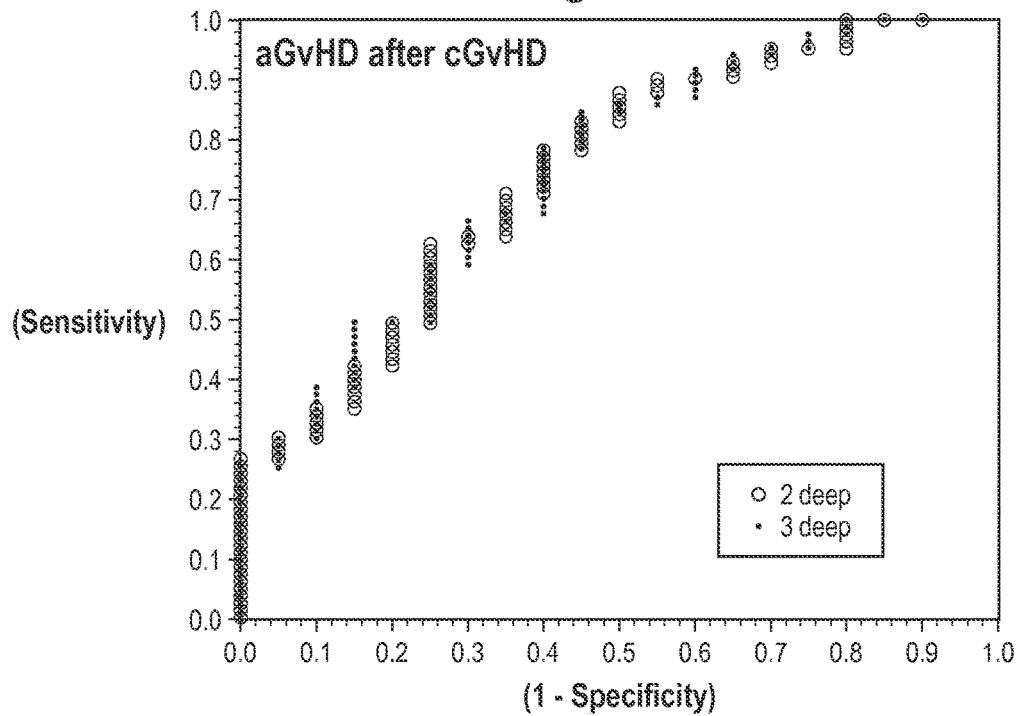
FIGS. 3A-3D are ROC curves for the top 100 features as selected by t-test for the four clinical questions when traversing the space of pairs of features and single features ('2 deep') used in the mini-classifiers of the classifiers developed for FIG. 2, and the space of triplets and pairs of features and single features used in the mini-classifiers.
Figure 3B:
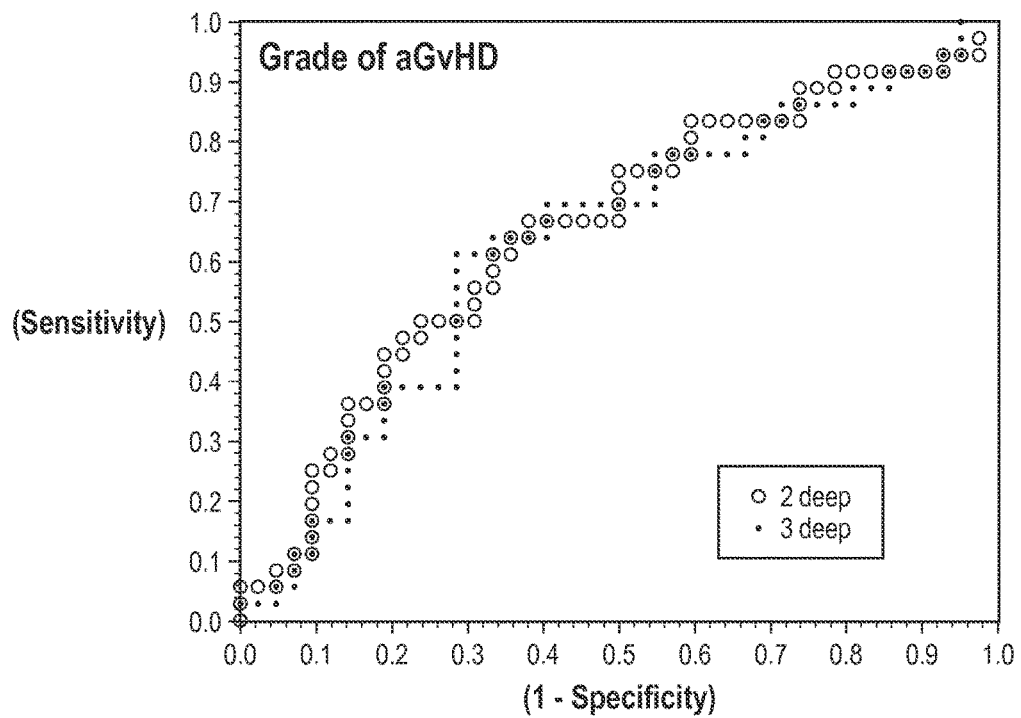
Figure 3C:
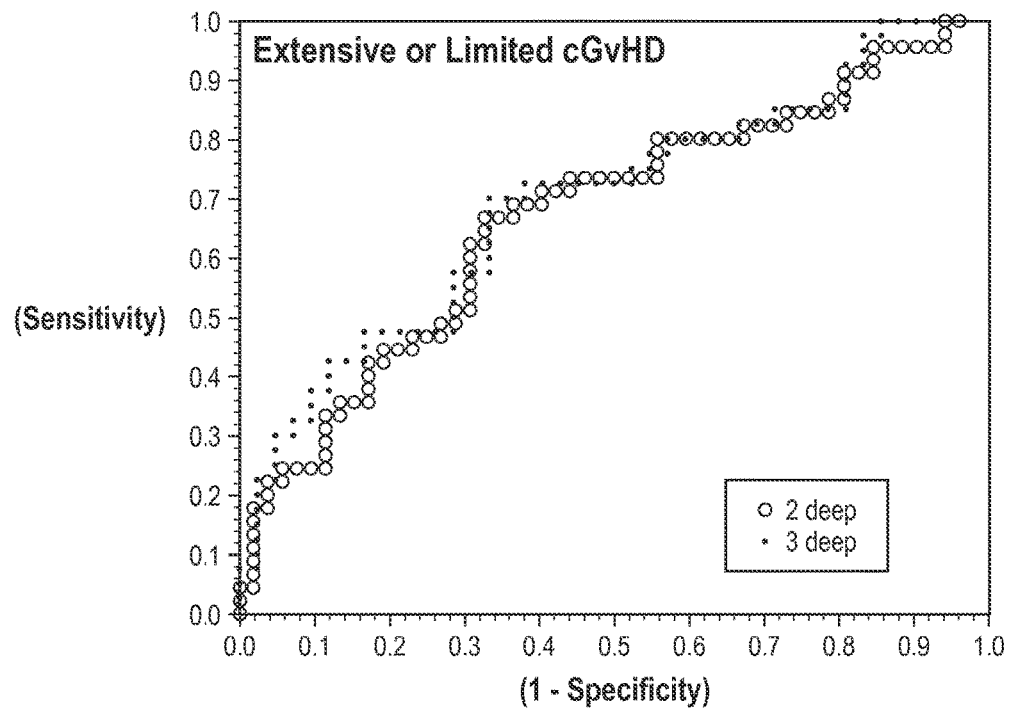
Figure 3D:
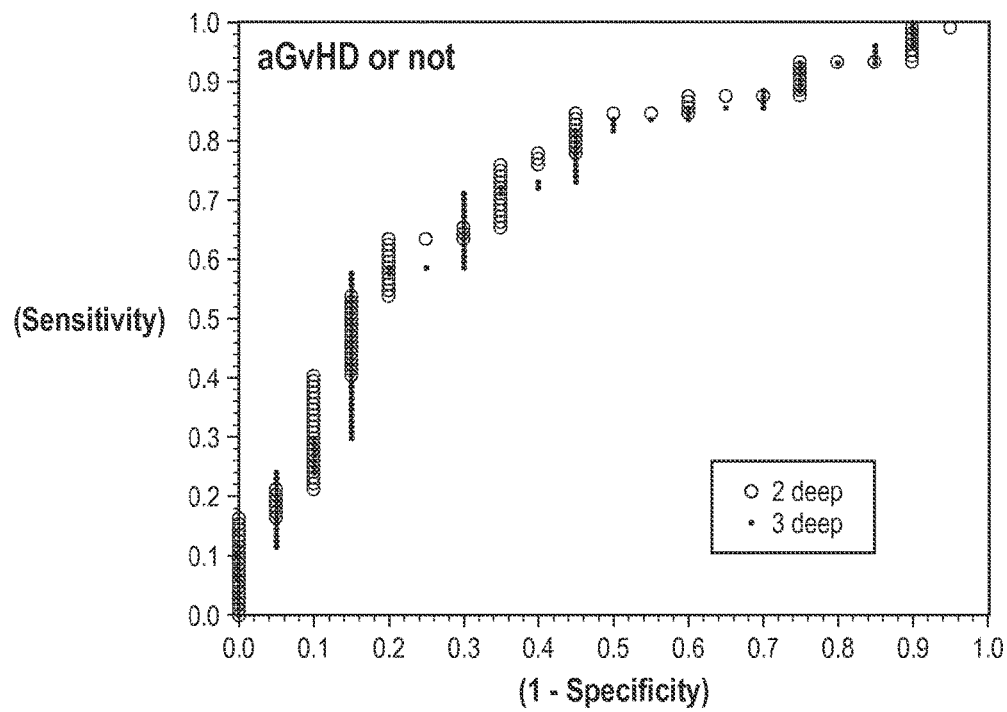

A method for assessing the risk of a patient receiving a transplant of pluripotent hematopoietic stem cells (PHSC) or bone marrow developing GvHD or characterizing the disease is disclosed. The method makes use of mass spectrometry data obtained from a blood-based sample obtained from the patient post-transplant. The method also makes use of a computer configured as a classifier which operates to classify the mass spectrometry data with the aid of a reference set of class-labeled mass spectrometry data obtained from a plurality of blood-based samples from other patients who received a PHSC or bone marrow transplant.

The methodology we describe in this document makes use of a MALDI-TOF mass spectrometry method in which the blood-based sample is subject to at least 100,000 laser shots. This methodology allows greater spectral information to be obtained from the sample than normally acquired using standard dilute and shoot MALDI-TOF methods, which typically use only ~1000 to 2000 shots. The methodology preferably makes use of the so-called "deep MALDI" mass spectrometry technique described in U.S. Patent application of H. Röder et al., Ser. No. 13/836,436 filed Mar. 15, 2013, US patent application publication no. 2013/0320203, the contents of which are incorporated by reference herein. This methodology will be described in some detail in the following detailed description and the discussion of FIG. 5 later in this document.

The method continues with a step of operating on the mass spectral data with a programmed computer implementing a classifier configured as a combination of filtered mini-classifiers using a regularized combination method. This step includes the use of what we have termed "CMC/D" classifiers (Combination of Mini-Classifiers with Dropout regularization), as described in pending U.S. patent application of H. Röder et al., Ser. No. 14/486,442 filed Sep. 15, 2014, U.S. patent application publication 2015/0102216, the content of which is incorporated by reference herein. The method of generating a CMC/D classifier and using it to generate a class label to predict or characterize graft-versus-host disease is described in detail below. This method of generating the classifier from a development set of sample data (mass spectrometry data) will be discussed below in conjunction with FIG. 1.

In the operating step, the classifier compares the integrated intensity values with feature values of a reference set of class-labeled mass spectral data obtained from a multitude of patients having received a transplant of PHSC or bone marrow and generating a class label for the sample. This step may make use of a classification algorithm such as k-nearest neighbor (KNN), selecting a class label by majority vote of the nearest neighbors in a multidimensional feature space. The class label is associated with the risk of a patient providing the sample developing GvHD or characterizing the GvHD, e.g., staging the disease or predicting whether cGvHD will follow aGvHD. The reference set of class-labeled mass spectral data may take the form of a development set used to develop the classifier, or may take the form of some subset of the development set.

In one embodiment, the final class label that is reported may take the form of a panel of class labels associated with the sample, each class label associated with a different clinical question in regards to GvHD. In this embodiment, the operating step is performed multiple times by different classifiers, each configured as a combination of filtered mini-classifiers using a regularized combination method and addressing a different clinical question associated with the development or characterization of GvHD. The method then generates a panel (or set) of class label results, one for each operating step/clinical question.

In one possible embodiment, one of the classifiers addresses the clinical question of whether the patient is likely to develop aGvHD. In another embodiment, one of the classifiers addresses the clinical question of whether the patient is likely to develop aGvHD at grade II or higher as compared to not developing aGvHD or developing aGvHD disease only at grade 1. In another embodiment, one of the classifiers addresses the clinical question of whether the patient is likely to develop cGvHD after developing aGvHD.

We also describe the mass spectrometry features (m/z ranges) which are used for classification. The use of deep MALDI mass spectrometry reveals hundreds of potential features for classification (i.e., features at which integrated intensity values are obtained from the spectrum under test and features for which integrated intensity values are stored from the reference set). In one embodiment, the integrated intensity values are obtained from at least 50 features listed in Appendix A, such as 50 features, 100 features or 200 or more features.

Our work in discovering the classifier and methodology of predicting or characterizing GvHD occurred as a result of conducting mass spectrometry on a set of blood-based samples from patients receiving either a PHSC or bone marrow transplant. This study, and the samples we used, will be described first. Then we will describe our methodology of creating the classifier and its use to predict or characterize GvHD in patients receiving PHSC or bone marrow transplants. The description will further describe performance characteristics of a variety of classifiers we created. Later, this document will describe a representative practical testing environment in which the invention can be practiced, for example in a laboratory setting as a fee-for-service.

The Study and Samples

Blood-based samples (serum or plasma) were obtained from 124 patients receiving a bone marrow or PHSC transplant, along with matched clinical data. Five patients suffered neither acute nor chronic GvHD, 15 patients had de novo cGvHD, 21 had aGvHD but not cGvHD and 83 had both acute and chronic GvHD. Some relevant clinical characteristics for these patients are summarized in table 1.

TABLE 1

Patient Characteristics

| | | No GvHD N = 5 | aGvHD only N = 21 | cGvHD only N = 15 | aGvHD and cGvHD N = 83 |
|---|---|---|---|---|---|
| aGvHD Grade | I | | 9 | | 44 |
| | II | | 12 | | 31 |
| | III | | 0 | | 5 |
| | IV | | 0 | | 3 |
| cGvHD Classification | Extensive | | | 5 | 41 |
| | Limited | | | 10 | 42 |
| Transplant Type | PHSC | 4 | 15 | 15 | 71 |
| | Bone marrow | 1 | 6 | 0 | 12 |
| Donor | Sibling | 1 | 11 | 6 | 22 |
| | Matched unrelated donor | 4 | 10 | 9 | 61 |
| HLA matched | Yes | 3 | 12 | 12 | 63 |
| | No | 2 | 9 | 3 | 20 |
| Age | Median | 57 | 51 | 39 | 48 |
| | Range | 40-65 | 39-65 | 19-67 | 18-70 |
| Diagnosis | ALL | 0 | 1 | 1 | 9 |
| | AML (AML/MF) | 2 | 9 | 8 | 38 |
| | CLL | 0 | 1 | 0 | 2 |
| | CML | 0 | 1 | 1 | 10 |
| | CMML | 0 | 2 | 0 | 3 |
| | MDS | 2 | 1 | 1 | 7 |
| | MM | 0 | 2 | 0 | 3 |
| | MCL | 0 | 0 | 1 | 1 |
| | NHL (NHL/MCL) | 1 | 3 | 2 | 5 |
| | NPL | 0 | 0 | 0 | 1 |
| | OMF | 0 | 1 | 1 | 3 |
| | SAA | 0 | 0 | 0 | 1 |
| GvHD Prophylaxis | cyclosporine + methotrexate | 3 | 18 | 10 | 75 |
| | Other | 2 | 3 | 5 | 8 |

Abbreviations: HLA = human leukocyte antigen, ALL = acute lymphoblastic leukemia, AML = acute myelogenous leukemia, MF = mycosis fungoides, CLL = chronic lymphocytic leukemia, CML = chronic myelogenous leukemia, CMML = chronic myelomonocytic leukemia, MDS = myelodysplastic syndrome, MM = multiple myeloma, MCL = mantel cell lymphoma, NHL = non-Hodgkin's lymphoma, NPL = neoplasm, OMF = osteomyelofibrosis, SAA = severe aplastic anemia Given the samples and clinical data available in this project, classifiers were developed to answer each of these clinical questions:

A. Is it possible to differentiate patients who will only develop aGvHD from those who will suffer from both aGvHD and cGvHD?

B. Is it possible to identify which patients will experience aGvHD at grade II or higher from those who will not get GvHD at all or suffer from aGvHD only at grade I?

C. Is it possible to identify patients who will experience limited cGvHD from those who experience extensive cGvHD?

D. Is it possible to identify patients who will develop aGvHD (with or without subsequent cGvHD)?

Spectral Acquisition

Our method makes use of mass spectrometry, and in particular Matrix Assisted Laser Desorption and Ionization-Time of Flight (MALDI-TOF) mass spectrometry. Since we wanted to probe deeply into the protein content of the serum or plasma of the patient samples, we used the techniques of deep-MALDI as described in the previously-cited patent application of H. Röder et al. The spectral acquisition will be described in this section.

The blood-based samples were thawed and 3 µl aliquots of each patient sample and quality control serum (a pooled sample obtained from serum from five healthy patients purchased from ProMedDx) spotted onto cellulose serum cards (Therapak). The cards were allowed to dry for 1 hour at ambient temperature after which the whole serum spot was punched out with a 6 mm skin biopsy punch (Acuderm). Each punch was placed in a centrifugal filter with 0.45 µm nylon membrane (VWR). One hundred µl of HPLC grade water (JT Baker) was added to the centrifugal filter containing the punch. The punches were vortexed gently for 10 minutes then spun down at 14,000 rcf (relative centrifugal force) for 2 minutes. The flow-through was removed and transferred back on to the punch for a second round of extraction. For the second round of extraction, the punches were vortexed gently for 3 minutes then spun down at 14,000 rcf for 2 minutes. Twenty microliters of the filtrate from each sample was then transferred to a 0.5 ml eppendorf tube for MALDI analysis.

All subsequent sample preparation steps were carried out in a custom designed humidity and temperature control chamber (Coy Laboratory). The temperature was set to 30° C. and the relative humidity at 10%.

An equal volume of freshly prepared matrix (25 mg of sinapinic acid dissolved in 1 ml of 50% acetonitrile:50% water plus 0.1% TFA) was added to each 20 µl serum extract and the mix vortexed for 30 sec. The first two aliquots (2×2 µl) of sample:matrix mix were discarded into the tube cap. Four aliquots of 2 µl sample:matrix mix were then spotted onto a polished steel MALDI target plate (Bruker Daltonics). The MALDI target was allowed to dry in the chamber before placement in a MALDI-TOF mass spectrometer ((Ultraflextreme, Bruker Daltonics, Bremen Germany).

This set of samples (137 patient samples plus QC sample) was processed for MALDI analysis in 4 batches. Four preparations of the QC sample were added to the beginning (2 preparations) and end (2 preparations) of each batch run.

Acquisition of Mass Spectra

MALDI spectra were obtained using the MALDI-TOF mass spectrometer mentioned above, equipped with a 2000 Hz SmartBeam laser. Data were acquired with positive ion detection in linear mode with the following settings: accelerating voltage set to 25 kV, extraction voltage set to 23.15 kV, lens voltage set to 7 kV, and the delayed extraction time set to 200 ns. The instrument was externally calibrated using the Bruker Protein Standard Mix consisting of insulin, ubiquitin, cytochrome c, and myoglobin.

Eight hundred shot spectra were collected from 63 pre-defined positions per MALDI spot (63×800×3 spots per sample), for a total of 151,200 laser shots per sample. While in this example 151,200 shots were done so that 189 (63×3) 800-shot spectra were acquired, we believe that suitable deep spectral information would be obtained as long as good quality spectra from at least 100,000 laser shots can be averaged. It would be possible to obtain spectra averaged from an even greater number of shots, such as 500,000 or 1,000,000 shots, using the techniques of the deep-MALDI patent application cited previously. Fuzzy control for laser power was turned off. No evaluation criteria were used to filter out spectra during acquisition. All filtering and processing of spectra was done post-acquisition.

Spectral Pre-Processing

As is customary and known in the art, we used spectral pre-processing routines described in this section on the spectra acquired as described above. These include background subtraction, alignment, normalization, averaging and batch correction.

Background Subtraction, Alignment, Normalization and Averaging of Spectra to Produce One Spectrum Per Sample There were 189 800-shot replicate spectra available for each patient acquired using deep MALDI instrument settings. The spectra were filtered using a ripple filter to remove artificial noise resulting from the digital converter. The background was subtracted for the purpose of finding peaks to be used in alignment. Background subtraction methods are known, see e.g., U.S. Pat. No. 7,736,905 assigned to Biodesix, Inc., the content of which is incorporated by reference herein. The threshold for peak detection was set to a signal to noise ratio of 6. The raw spectra (no background subtraction) were then aligned using the calibration points listed in table 2 to remove slight differences in peak m/z. Only spectra with a minimum of 15 peaks detected and having used 5 alignment points were considered for inclusion in the average. As it is not known how many spectra will pass these requirements for each sample, 134 spectra were selected at random to include in the average resulting in an average spectra of approximately 107K shots (134× 800).

TABLE 2

Calibration points used to align the raw spectra prior to averaging

| | m/z |
|---|---|
| 1 | 3318 |
| 2 | 4157 |
| 3 | 6441 |
| 4 | 6843 |
| 5 | 6887 |
| 6 | 6947 |
| 7 | 8211 |
| 8 | 8698 |
| 9 | 8819 |
| 10 | 9737 |
| 11 | 9721 |
| 12 | 9943 |
| 13 | 11509 |
| 14 | 13773 |
| 15 | 13895 |
| 16 | 14053 |
| 17 | 15141 |
| 18 | 17398 |
| 19 | 21084 |
| 20 | 28107 |

Preprocessing of Averaged Spectra

The spectra were background subtracted, fine-tune calibrated using the calibration points listed in table 3, and normalized using a partial ion current (PIC) window from 3500-23,000 Da. Partial ion current normalization is described in U.S. Pat. No. 7,736,905 and so a further detailed description is omitted for the sake of brevity.

TABLE 3

Calibration points used to align the averaged spectra

| | m/z |
|---|---|
| 1 | 3316 |
| 2 | 4157 |
| 3 | 4189 |
| 4 | 4462 |
| 5 | 4715 |
| 6 | 6440 |
| 7 | 6639 |
| 8 | 6662 |
| 9 | 6846 |
| 10 | 7573 |
| 11 | 7943 |
| 12 | 8215 |
| 13 | 8694 |
| 14 | 8821 |
| 15 | 8926 |
| 16 | 9141 |
| 17 | 9721 |
| 18 | 12876 |
| 19 | 13775 |
| 20 | 13895 |
| 21 | 14053 |
| 22 | 14102 |
| 23 | 15141 |
| 24 | 15882 |
| 25 | 17268 |
| 26 | 18643 |
| 27 | 28107 |
| 28 | 28206 |

Feature Definitions

Feature definitions were selected by viewing (manually) the GvHD spectral averages simultaneously and selecting the left and right boundaries by assessing the spread of the band for a given feature. This process should capture the feature widths adequately for any individual spectrum. A total of 241 features (m/z ranges or peaks) were identified as being useful for classification and a list of such features is found in Appendix A. The feature definitions were applied to each sample spectrum to create a feature table of feature values (integrated intensity values of each of the features).

Analysis of Reference Samples by Batch

Four preparations of SerumP2 (quality control sample) were prepared along with the experimental samples in each batch. Two of these preparations were plated at the beginning and the other two at the end of the batch of the experimental samples. The purpose of the SerumP2 samples was to provide a common reference sample in each batch that can be used to correct the batches for expected day to day fluctuations in spectral acquisition. The SerumP2 samples were averaged and preprocessed as described above.

Next, the SerumP2 from each batch were compared to look for systematic m/z sensitivity deviation between batches. As the features of high, medium, and low intensities may not be systematically different in the same way, separate correction functions were found for each intensity range.

Batch1 was used as the baseline such that batches 2-4 were corrected to batch1. For each intensity range, the ratios of feature values were found by dividing Batch 2-4 by Batch 1. These ratios were plotted as a function of m/z. The slope and intercept were found for each range and for each batch. A table containing the slopes and intercepts for each range and batch can be found in Appendix B of our prior provisional application (see Priority section of this document), the content of which is incorporated by reference herein.

Batch Correction

Using the slope and intercept found for high, med, and low intensity features for batches 2-4, correction coefficients (CoE) were found for each m/z feature using a linear function. For a given batch i (i=2, 3, 4) and intensity level x (x=low, med, high)

$CoE_{i,x} = slope_{i,x}(m/z) + intercept_{i,x}$

These correction coefficients were then used to correct all samples including SerumP2 and the GvHD samples from batches 2-4 by dividing the feature value by the correction coefficient. For batch i and a feature of feature intensity x:

Batch $i,x$/Batch $1,x = slope_{i,x}(m/z) + intercept_{i,x}$

Batch $i,x = CoE_{i,x}$(Batch1)

The correct coefficient to use was dependent on whether the feature value belonged to the high, med, or low range. Following correction, the slope was re-examined by plotting the ratio of $Batch_{2-4}$/Batch1 versus m/z as before. Application of the correction coefficient should bring the slope closer to zero and intercept closer to one indicating that the systematic deviations between batches have been minimized. We created plots as described above to analyze the behavior of the plots before and after correction for SerumP2 in batch 2. The plots (not shown) indicate that, post-correction, the plots have a Y intercept very near to 1 (~0.98-0.99) and a slope of 0.000001, whereas before correction the plots had a Y intercept of between 0.85 and 1.16 and a non-negligible slope, indicating the batch correction removed the day-to-day fluctuating systematic error in spectral acquisition for the low, medium and high spectral features.

Normalization

Using the corrected feature table (per the batch correction described above), features were examined to find regions of intrinsic stability to use as normalization windows. To normalize, the values of the listed features were summed to find the normalization factor for each sample. All feature values were then divided by the normalization factor to arrive at the final feature table (integrated intensity values) used in CMC/D classifier generation for each of the features listed in Appendix A.

TABLE 4

Features used for normalization windows

| Left m/z | Left m/z | Right m/z |
|---|---|---|
| 3132 | 3123.35 | 3139.84 |
| 3398 | 3385.17 | 3409.96 |
| 3468 | 3458.17 | 3478.14 |
| 3558 | 3542.23 | 3574.13 |
| 3685 | 3670.79 | 3698.32 |
| 3759 | 3748.68 | 3768.43 |
| 3779 | 3768.49 | 3790.16 |
| 3800 | 3790.37 | 3808.99 |
| 3910 | 3903.06 | 3917.40 |
| 3957 | 3946.84 | 3967.65 |
| 4639 | 4619.08 | 4659.58 |
| 4943 | 4932.51 | 4954.13 |
| 5110 | 5095.81 | 5125.16 |
| 5415 | 5399.59 | 5427.44 |
| 5563 | 5541.28 | 5584.33 |
| 6015 | 6004.45 | 6025.22 |
| 6036 | 6025.52 | 6046.89 |

TABLE 4-continued

| Features used for normalization windows | | |
|---|---|---|
| Left m/z | Left m/z | Right m/z |
| 6706 | 6695.41 | 6716.67 |
| 6737 | 6717.08 | 6756.88 |
| 10543 | 10526.57 | 10558.89 |
| 10591 | 10567.31 | 10613.74 |
| 20945 | 20877.65 | 21012.85 |
| 21074 | 21013.33 | 21134.02 |

CMC/D Classifier Generation Method

The new classifier development process using the method of combination of mini-classifiers (mCs) with dropout (CMC/D) is shown schematically in FIG. 1. The steps in this process are explained in detail below. The methodology, its various advantages, and several examples of its use, are explained in great detail in U.S. patent application Ser. No. 14/486,442 filed Sep. 15, 2014, the content of which is incorporated by reference. A brief explanation of the methodology will be provided here first, and then illustrated in detail in conjunction with FIG. 1 for the generation of the GvHD classifiers.

In contrast to standard applications of machine learning focusing on developing classifiers when large training data sets are available, the big data challenge, in bio-life-sciences the problem setting is different. Here we have the problem that the number (n) of available samples, arising typically from clinical studies, is often limited, and the number of attributes (p) per sample usually exceeds the number of samples. Rather than obtaining information from many instances, in these deep data problems one attempts to gain information from a deep description of individual instances. The present methods take advantage of this insight, and is particularly useful, as here, in problems where $p \gg n$.

The method includes a first step a) of obtaining measurement data for classification from a multitude of samples, i.e., measurement data reflecting some physical property or characteristic of the samples. The data for each of the samples consists of a multitude of feature values, and a class label. In this example, the data takes the form of mass spectrometry data, in the form of feature values (integrated peak intensity values at a multitude of m/z ranges or peaks) as well as a label indicating some attribute of the sample (patient had aGvHD, cGvHD after aGvHD, cGvHD at a specific level, etc.). In this example, the class labels were assigned by a human operator to each of the samples after investigation of the clinical data associated with the sample.

The method continues with a step b) of constructing a multitude of individual mini-classifiers using sets of feature values from the samples up to a pre-selected feature set size s (s=integer 1 . . . n). For example a multiple of individual mini- or atomic classifiers could be constructed using a single feature (s=1), or a pair of features (s=2), or three of the features (s=3), or even higher order combinations containing more than 3 features. The selection of a value of s will normally be small enough to allow the code implementing the method to run in a reasonable amount of time, but could be larger in some circumstances or where longer code run-times are acceptable. The selection of a value of s also may be dictated by the number of measurement data values (p) in the data set, and where p is in the hundreds, thousands or even tens of thousands, s will typically be 1, or 2 or possibly 3, depending on the computing resources available. The mini-classifiers execute a supervised learning classification algorithm, such as k-nearest neighbors, in which the values for a feature or pairs of features of a sample instance are compared to the values of the same feature or features in a reference set and the nearest neighbors (e.g., k=5) in an s-dimensional feature space are identified and by majority vote a class label is assigned to the sample instance for each mini-classifier. In practice, there may be thousands of such mini-classifiers depending on the number of features which are used for classification.

The method continues with a filtering step c), namely testing the performance, for example the accuracy, of each of the individual mini-classifiers to correctly classify at least some of the multitude of samples, or measuring the individual mini-classifier performance by some other metric (e.g. the difference between the Hazard Ratios (HRs) obtained between groups defined by the classifications of the individual mini-classifier for the training set samples) and retaining only those mini-classifiers whose classification accuracy, predictive power, or other performance metric, exceeds a pre-defined threshold to arrive at a filtered (pruned) set of mini-classifiers. The class label resulting from the classification operation may be compared with the class label for the sample known in advance if the chosen performance metric for mini-classifier filtering is classification accuracy. However, other performance metrics may be used and evaluated using the class labels resulting from the classification operation. Only those mini-classifiers that perform reasonably well under the chosen performance metric for classification are maintained. Alternative supervised classification algorithms could be used, such as linear discriminants, decision trees, probabilistic classification methods, margin-based classifiers like support vector machines, and any other classification method that trains a classifier from a set of labeled training data.

To overcome the problem of being biased by some univariate feature selection method depending on subset bias, we take a large proportion of all possible features as candidates for mini-classifiers. We then construct all possible KNN classifiers using feature sets up to a pre-selected size (parameter s). This gives us many "mini-classifiers": e.g. if we start with 100 features for each sample (p=100), we would get 4950 "mini-classifiers" from all different possible combinations of pairs of these features (s=2), 161,700 mini-classifiers using all possible combination of three features (s=3), and so forth. Other methods of exploring the space of possible mini-classifiers and features defining them are of course possible and could be used in place of this hierarchical approach. Of course, many of these "mini-classifiers" will have poor performance, and hence in the filtering step c) we only use those "mini-classifiers" that pass predefined criteria. These criteria are chosen dependent on the particular problem: If one has a two-class classification problem, one would select only those mini-classifiers whose classification accuracy exceeds a pre-defined threshold, i.e., are predictive to some reasonable degree. Even with this filtering of "mini-classifiers" we end up with many thousands of "mini-classifier" candidates with performance spanning the whole range from borderline to decent to excellent performance.

The method continues with step d) of generating a master classifier by combining the filtered mini-classifiers using a regularized combination method. In one embodiment, this regularized combination method takes the form of repeatedly conducting a logistic training of the filtered set of mini-classifiers to the class labels for the samples. This is done by randomly selecting a small fraction of the filtered mini-classifiers as a result of carrying out an extreme dropout from the filtered set of mini-classifiers (a technique referred to as drop-out regularization herein), and conducting logistical training on such selected mini-classifiers. While similar in spirit to standard classifier combination methods (see e.g. S. Tulyakov et al, *Review of Classifier Combination Methods*, Studies in Computational Intelligence, Volume 90, 2008, pp. 361-386), we have the particular problem that some "mini-classifiers" could be artificially perfect just by random chance, and hence would dominate the combinations. To avoid this overfitting to particular dominating "mini-classifiers", we generate many logistic training steps by randomly selecting only a small fraction of the "mini-classifiers" for each of these logistic training steps. This is a regularization of the problem in the spirit of dropout as used in deep learning theory. In this case, where we have many mini-classifiers and a small training set we use extreme dropout, where in excess of 99% of filtered mini-classifiers are dropped out in each iteration.

In more detail, the result of each mini-classifier is one of two values, either "Class 1" or "Class 2" in this example. We can then use standard logistic regression to combine the results of the mini-classifiers by defining the probability of obtaining a "Class 1" label (see e.g. the Wikipedia page on logistic regression)

$$P(\text{``Class 1''}|\text{feature for a spectrum}) = \frac{\exp\left(\sum_{mini\ classifiers}^{w_{mc}} I(mc(\text{feature values}))\right)}{\text{Normalization}} \qquad \text{Eq. (1)}$$

where $I(mc(\text{feature values}))=1$, if the mini-classifier mc applied to the feature values of a sample returns "Class 1", and 0 if the mini-classifier returns "Class 2". The weights for each mini-classifier, $w_{mc}$, are unknown and need to be determined from a regression fit of the above formula for all samples in the training set using +1 for the left hand side of the formula for the Class 1-labeled samples in the training set, and 0 for the Class 2-labeled samples, respectively. As we have many more mini-classifiers, and therefore weights, than samples, typically thousands of mini-classifiers and only tens of samples, such a fit will always lead to nearly perfect classification, and can easily be dominated by a mini-classifier that, possibly by random chance, fits the particular problem very well. We do not want our final test to be dominated by a single special mini-classifier which only performs well on this particular set and is unable to generalize well. Hence we designed a method to regularize such behavior: Instead of one overall regression to fit all the weights for all mini-classifiers to the training data at the same time, we use only a few of the mini-classifiers for a regression, but repeat this process many times in generating the master classifier. For example we randomly pick three of the mini-classifiers, perform a regression for their three weights, pick another set of three mini-classifiers, and determine their weights, and repeat this process many times, generating many random picks, i.e. realizations of three mini-classifiers. The final weights defining the CMC/D master classifier are then the averages of the weights over all such realizations. The number of realizations should be large enough that each mini-classifier is very likely to be picked at least once during the entire process. This approach is similar in spirit to "drop-out" regularization, a method used in the deep learning community to add noise to neural network training to avoid being trapped in local minima of the objective function.

Other methods for performing the regularized combination method in step (d) that could be used include:

Logistic regression with a penalty function like ridge regression (based on Tikhonov regularization, Tikhonov, Andrey Nikolayevich (1943).

"Об устойчивости обратных задач" [On the stability of inverse problems]. Doklady Akademii Nauk SSSR 39 (5): 195-198.)

The Lasso method (Tibshirani, R. (1996). Regression shrinkage and selection via the lasso. J. Royal. Statist. Soc B., Vol. 58, No. 1, pages 267-288).

Neural networks regularized by drop-out (Nitish Shrivastava, "Improving Neural Networks with Dropout", Master's Thesis, Graduate Department of Computer Science, University of Toronto; available online from the computer science department website of the University of Toronto, see prior provisional for link.

General regularized neural networks (Girosi F. et al, Neural computation, (7), 219 (1995).

The above-cited publications are incorporated by reference herein. Our approach of using drop-out regularization has shown promise in avoiding over-fitting, and increasing the likelihood of generating generalizable tests, i.e. tests that can be validated in independent sample sets.

In step e) of the method, the set of samples is randomly separated into a test set and a training set, and the steps b)-d) are repeated in the programmed computer for different realizations of the separation of the set of samples into test and training sets, thereby generating a plurality of master classifiers, one for each realization of the separation of the set of samples into training and test sets.

The method continues with step f) of defining a final classifier from one or a combination of more than one of the plurality of master classifiers. In the present example, the final classifier is defined as a majority vote of all the master classifiers resulting from each separation of the sample set into training and test sets.

With reference now to FIG. 1, we have a development sample set 100, in this case the mass spectrometry data of the 124 patients provided in the study.

At step 102, the definition of the groups (class labels) is assigned. The first step in constructing a new classifier is to decide on an appropriate way of identifying candidate reference sets to use for the classifiers. This needs to be established for each separate classification problem (clinical question) attempted with the dataset. For the four clinical questions outlined above, the reference class definitions are summarized in table 5. In this instance, the "class labels" or class definitions defined at step 102 are "reference class 1" or simply "Class 1" in the following discussion and "reference class 2" or "Class 2" as indicated at 104 and 106. (It will be appreciated from the following discussion that classifiers were generated in accordance with FIG. 1 for each of the four clinical questions shown in Table 5)

TABLE 5

Reference Class Definitions

| Clinical Question | Reference Class 1 | Reference Class 2 |
|---|---|---|
| A. cGvHD or not post aGvHD | Patients with aGvHD but no cGvHD (N = 21) | Patients with both aGvHD and cGvHD (N = 83) |

TABLE 5-continued

Reference Class Definitions

| Clinical Question | | Reference Class 1 | Reference Class 2 |
|---|---|---|---|
| B. | Grade of aGvHD | Patients with no GvHD or aGvHD of grade I. Only patients with PHSC transplant and CSA + MTX prophylaxis | Patients with aGvHD of grade II or higher. Only patients with PHSC transplant and CSA + MTX prophylaxis |
| C. | Extent of cGvHD | Patients with limited cGvHD | Patients with extensive cGvHD |
| D. | aGvHD or not | Patients with no aGvHD (N = 20) | Patients with aGvHD (N = 104) |

At step 108, the samples were then split into training and test sets. This is described in more detail below.

At step 112, the training set was subject to steps 120, 126, 130. As shown at 124, the training set includes feature values at specified m/z ranges (see Appendix A). In step 120, the KNN mini-classifiers compare the feature values (124) in multidimensional feature space shown schematically at 122. In this example, the value for parameter s was 2 or 3, as explained in the following discussion.

Creation and Filtering of Mini-Classifiers (Steps 120, 126)

Once the initial class definition of the development set has been established, the development set 100 is split into training and test sets 112 and 110, respectively. Many K-nearest neighbor (KNN) mini-classifiers (mCs) that use the training set as their reference set are constructed at step 120 using single features or pairs of features from the 241 mass spectral features already identified and listed in Appendix A. For 241 features, this amounts to considering 29,161 possible mCs. The parameters used to traverse the space of mCs for this project are listed in table 6.

TABLE 6

Parameters used to create mCs

| KNN parameters | |
|---|---|
| K | 5-11, depending on training set size |
| mC traversal parameters | |
| Max number of features (s) | 2 or 3 |

To target a final classifier that has certain performance characteristics, these mCs are filtered in step 126. Each mC is applied to its training set 112 and performance metrics are calculated from the resulting classifications of the training set. Only mCs that satisfy thresholds on these performance metrics pass filtering to be used further in the process. The mCs that fail filtering are discarded. For this project only classification accuracy filtering was used, i.e., the classifier was applied to the training set 112 and the accuracy of the resulting classification had to lie within a preset range for the mC to pass filtering. The filtering options used in this project are listed in table 7. In table 7, it will be noted that we created different classifiers for different clinical questions, these classifiers are denoted by "Study #". As far as the number of features used, it will be noted also that in some of the studies we used a sub-set of all the possible m/z features of Appendix A, namely those features that were selected for statistical significance using t-test as explained in the following discussion.

TABLE 7

Summary of mC filtering options used

| Study # | Clinical Question | # features used |
|---|---|---|
| 1 | cGvHD after aGvHD? | 241 |
| 2 | cGvHD after aGvHD? | 241 (narrower mC filtering) |
| 3 | cGvHD after aGvHD? | 100, as selected by t-test |
| 4 | Grade II or higher aGvHD? | 241 |
| 5 | Grade II or higher aGvHD? | 100, as selected by t-test |
| 6 | Extensive or limited cGvHD? | 241 |
| 7 | Extensive or limited cGvHD? | 100, as selected by t-test |
| 8 | aGvHD? | 241 |
| 9 | aGvHD? | 100, as selected by t-test |
| 10 | aGvHD? | 50, as selected by t-test |

Step 130 Generating Master Classifiers (MC) by Combination of Mini-Classifiers Using Logistic Regression with Dropout Once the filtering of the mCs is complete, the mCs are combined in one master classifier (MC) in step 130 using a logistic regression trained using the training set labels. To help avoid overfitting the regression is regularized using extreme drop out. This is indicated at box 132 in FIG. 1. All CMC/D classifiers we generated in the 10 studies of Table 7 randomly selected 10 of the mCs for inclusion in each logistic regression iteration and averaged weights ($w_{mc}$) for the mCs over 10,000 dropout iterations.

Training/Test Splits and Analysis of Master Classifier Performance (Step 134)

At step 134, the performance of each MC resulting from step 130 on the test set 110 is then evaluated. Then, as indicated at by the loop 135, the split of the reference groups 102 into training and test sets 110 and 112 is performed many times using a stratified randomization. Each training/test split produces a MC which can be applied to the split test set (110) to assess performance. The use of multiple training/test splits avoids selection of a single, particularly advantageous or difficult, training set for classifier creation and avoids bias in performance assessment from testing on a test set that could be especially easy or difficult to classify.

At step 136, the master classifier (MC) performance data across all the training/test set splits is then analyzed. To do this, performance characteristics of the MCs and their classification results are obtained, and analyzed according to any convenient statistical measure (see the following discussion). Step 140 is an optional step of redefining (flipping) the group labels for samples which persistently are misclassified. At step 144, a final test is defined, in this case as a majority vote of all the MCs that result from each realization of the separation of the development sample set into training and test sets (i.e., the MCs that result from step 130 after each iteration of loop 135) and for which the sample is not part of the training set 112, termed Modified Majority Vote or MMV herein.

In defining the final test at step 144, it will be appreciated that the output of the logistic regression that defines each MC (resulting at step 130) is a probability of being in one of the two training classes (class 1 or class 2). These MC outputs can be combined to make one resultant classifier in several ways.

Applying a cutoff (e.g. 0.5) to these probabilities, one can generate a binary classification label for a sample from each MC. These labels can then be combined in a majority vote to obtain one binary classification for a sample. When analyzing the performance of the classifier in the development set (steps 134 and 138) it is helpful to use a modified majority vote for samples which are used in training the classifier. For samples which are used in the training set of some of the training/test set split realizations, the modified majority vote (MMV) is defined as the majority vote of the MC labels over the MCs which do not have the sample in the training set. For samples which are never used in any training set, the modified majority vote and majority vote are identical.

The MC probabilities can be averaged to yield one average probability for a sample. When working with the development set, this approach can also be adjusted to average over MCs for which a given sample is not included in the training set, in an analogous way to the MMV procedure. These average probabilities can be used as the output of a classifier or a threshold can be applied to convert them into a binary classification.

In addition, the standard deviation of the MC probabilities can be calculated for a sample. This can potentially provide additional information as to the certainty or uncertainty that can be ascribed to the average probability of a sample. While not being useful for providing a direct classification of a sample, these outputs can be used when multiple classifiers are stacked.

The present CMC/D classifier generation method (FIG. 1) works best when the reference groups/classes in the training set (defined at step 102) are of approximately equal sizes. To achieve this in most of these studies it was necessary to sample the reference classes at different rates. For example, for the first clinical question of cGvHD after aGvHD, there were 21 subjects with only aGvHD and 83 subjects with aGvHD and cGvHD. Hence, while the first class (Class 1) was split 50/50 (or 1:1) between test and training set, the second class (Class 2) was split in the ratio 1:6, so that each training/test set realization (loop 135) had 12 Class 2 samples in the training set and 71 Class 2 samples in the test set. The test/training splits were carried out stratified by human leukocyte antigen (HLA) matching and taking account of the age of the subject. HLA matching involves comparing the many HLA markers (proteins) found on donor cells with those expressed in the recipient, and the quality of the match is a good predictor of transplant success. Hence, it is important to take account of this and patient age, another relevant factor in predicting transplant success and eventual outcome, when splitting the samples into test and training sets. For the clinical question of cGvHD after aGvHD an alternative approach was also carried out in which each subject with only aGvHD were matched with one subject with both aGvHD and cGvHD, based on HLA matching status, diagnosis and age. These pairs of subjects were then randomized into test and training groups.

One other advantage of these multiple training/test splits (loop 135 and reiteration of steps 120, 126 and 130) is that it allows for the refinement of the initial assignment of the class label for the reference groups in problems where these are not clear and it provides a method to carry out 'semi-unsupervised' learning. Here, the latter possibility was explored in the context of high or low grade aGvHD. The initial reference groups were set up for the low/high grade aGvHD as described in study #5 of table 7. After creating the MCs for this approach, the MCs were applied to all samples. The modified majority vote label (MMV) was determined for each sample, by taking the majority vote of the MCs for which the sample was not included in the training set. These MMV labels were used as the starting reference groups for the next stage of classifier generation, which was carried out by reselecting the top 100 features by lowest t-test p values for the new groupings and using the same CMC/D filtering parameters as for the first iteration of loop 142. This process can be thought of as swapping the reference grouping labels for samples that persistently classify incorrectly in the previous iteration of the CMC/D process. As this process is repeated over multiple iterations, with multiple swaps of reference group labels and reselection of the top 100 features, the classifications converge to those which are produced with very high accuracy from the MMV of the resulting MCs. This method determines a self-consistent system of classifier, classifications and selected features. Within three iterations, the MMV labels had almost converged, with a classification accuracy of 0.96, see bottom row of table 8. The resulting MMV classifications for this self-consistent arrangement are given in Appendix C of our prior provisional application (see Priority section above), the contents of which are incorporated by reference herein.

Results

The results of the classifier development approaches are summarized in table 8 and the plots shown in FIG. 2A-2L. These plots are ROC curves for the approaches of table 8. The open circle in the plots indicates the position of a 0.5 average probability cutoff. The shaded band indicates the 90% confidence interval on the curve as estimated by bootstrap over MCs where a sample is in the test set for each realization. Classification accuracy is given in terms of modified majority vote classification (i.e. accuracy over all MCs for which the sample to be classified is not included in the training set). In table 8, "Plot A" refers to FIG. 2A, "Plot B" refers to FIG. 2B, etc. (NB: there is no "Plot I", consistent with Table 8). "# realizations" means the number of separations of the development set into training and test sets (loop 135 in FIG. 1).

TABLE 8

Summary of MMV classifier performance and correspondence to ROC curves of FIG. 2

| Study # | Clinical question | # batches (>1 indicates label swapping) | # realizations | Classification accuracy | ROC plot (FIG. 2) |
|---|---|---|---|---|---|
| 1 | cGvHD after aGvHD? | 1 | 100 | Overall: 0.59 aGvHD only: 0.70 aGvHD + cGvHD: 0.57 | |
| 1 | cGvHD after aGvHD? | 1 | 200 | Overall: 0.56 aGvHD only: 0.70 aGvHD + cGvHD: 0.53 | |
| 1 | cGvHD after aGvHD? | 1 | 500 | Overall: 0.58 aGvHD only: 0.70 aGvHD + cGvHD: 0.55 | |
| 1 | cGvHD after aGvHD? | 1 | 900 | Overall: 0.56 aGvHD only: 0.70 aGvHD + cGvHD: 0.53 | Plot A |
| 1 | cGvHD after aGvHD? | 1 | 100 - but with matched reference class subjects | Overall: 0.54 aGvHD only: 0.80 aGvHD + cGvHD: 0.48 | Plot B |
| 2 | cGvHD after | 1 | 300 | Overall: 0.54 aGvHD only: 0.75 | Plot C |

TABLE 8-continued

Summary of MMV classifier performance and correspondence to ROC curves of FIG. 2

| Study # | Clinical question | # batches (>1 indicates label swapping) | # realizations | Classification accuracy | ROC plot (FIG. 2) |
|---|---|---|---|---|---|
| | aGvHD? | | | aGvHD + cGvHD: 0.49 | |
| 3 | cGvHD after aGvHD? | 1 | 100 | Overall: 0.58 aGvHD only: 0.75 aGvHD + cGvHD: 0.54 | |
| 3 | cGvHD after aGvHD? | 1 | 900 | Overall: 0.59 aGvHD only: 0.75 aGvHD + cGvHD: 0.55 | Plot D |
| 4 | Grade II or higher aGvHD? | 1 | 150 | Overall: 0.56 Low Grade: 0.64 High Grade: 0.47 | Plot E |
| 5 | Grade II or higher aGvHD? | 1 | 150 | Overall: 0.63 Low Grade: 0.67 High Grade: 0.58 | Plot F |
| 6 | Extensive or limited cGvHD? | 1 | 150 | Overall: 0.60‡ Limited: 0.62 Extensive: 0.58 | Plot G |
| 7 | Extensive or limited cGvHD? | 1 | 150 | Overall: 0.66‡ Limited: 0.67 Extensive: 0.65 | Plot H |
| 8 | aGvHD? | 1 | 150 | Overall: 0.58 aGvHD: 0.57 No aGvHD: 0.65 | Plot J |
| 9 | aGvHD? | 1 | 150 | Overall: 0.67 aGvHD: 0.65 No aGvHD: 0.75 | Plot K |
| 10 | aGvHD? | 1 | 150 | Overall: 0.68 aGvHD: 0.68 No aGvHD: 0.65 | Plot L |
| 5 | Grade II or higher aGvHD? | 2 | 150 | Overall: 0.86* "Low Grade": 0.90* "High Grade": 0.81* | |
| 5 | Grade II or higher aGvHD? | 3 | 150 | Overall: 0.96* "Low Grade": 0.98* "High Grade": 0.94* | |

*accuracy with respect to self-consistently defined group definitions, not group definitions drawn directly from the clinical data
‡Training and results evaluated on patients having both acute and chronic disease. Performance was similar on patients with chronic disease regardless of prior acute disease The most promising approaches for each clinical question used the top 100 features selected for that question by t-test. With only 100 features, it is possible to explore a deeper space of mCs, traversing the space of single features, and pairs and triplets of features. (For 100 features, this is a total of 166,750 mCs). The ROC curves for these '3 deep' analyses are shown together with the '2 deep' curves from FIG. 2 in FIG. 3.

The associations of the classifications obtained from the MMV of the third iteration of the semi-unsupervised learning approach with available clinical data were investigated. The results are given in Appendix D of our prior provisional application, which is incorporated by reference herein. Note that the p values given are not adjusted for multiple comparisons. The only significant association (unadjusted for multiple comparisons) was with the relation between donor and recipient. There was no sign of association between classification and HLA matching, however. There appears to be some residual correlation of classifications with grade of aGvHD overall and in certain organs, but this is not statistically significant, even unadjusted for multiple comparisons and the classifications were not able to reliably identify patients with serious grade aGvHD.

Visualization of Results t-Distributed Stochastic Neighbor Embedding (t-SNE) is a tool that allows the visualization of high-dimensional data in a 2D or 3D-map, capturing much of the local structure of the data while also revealing global structure (e.g., the presence of clusters at several scales). The method converts high-dimensional Euclidean distances between data points into Gaussian similarities. In the low-dimensional (2D or 3D) space, the same process is applied using a Student-t distribution instead of a Gaussian distribution to compute the similarity between pairs of points. Then, iteratively, the method seeks for a low-dimensional representation of the original data set that minimizes the mismatch between the similarities computed in the high- and low-dimensional spaces. In this way, a 2D or a 3D point map is constructed that allows the visualization and identification of structure in a given dataset.

FIG. 4 shows t-SNE plots for classifiers addressing the four clinical questions of this study. In particular, FIGS. 4A-4I are pairs of t-SNE plots. The first plot of each pair is for class labels used for classifier development, and the second of each pairs is for the resulting classifier output classifications. FIG. 4A and FIG. 4B are for the occurrence of cGvHD or not post aGvHD (study #2), FIG. 4C and FIG. 4D are for grade of aGvHD (study #4), FIG. 4E and FIG. 4F are for severity of cGvHD (study #7), and FIG. 4G and FIG. 4H are for occurrence of aGvHD (study #9). FIG. 4I shows the classifications obtained from the semi-unsupervised learning approach applied to study #5. In the plots, A and B are the two coordinates of the t-SNE low dimensional space.

Figure 4A:
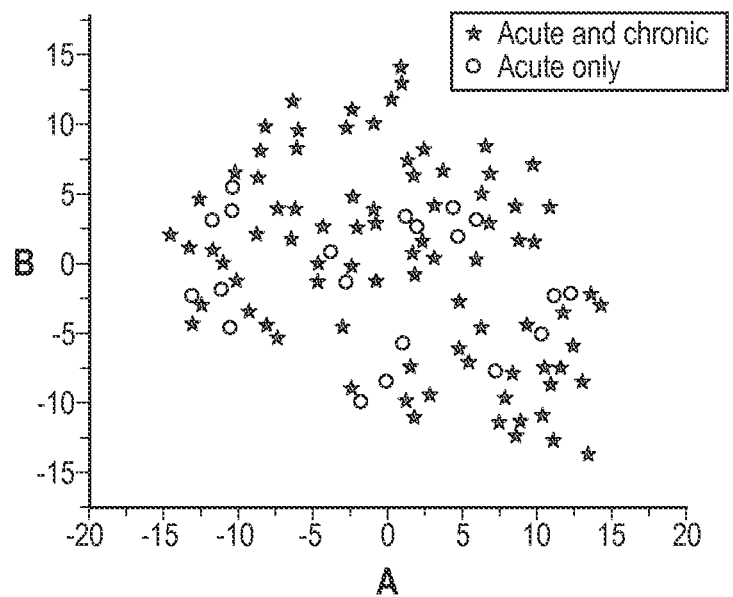
Figure 4B:
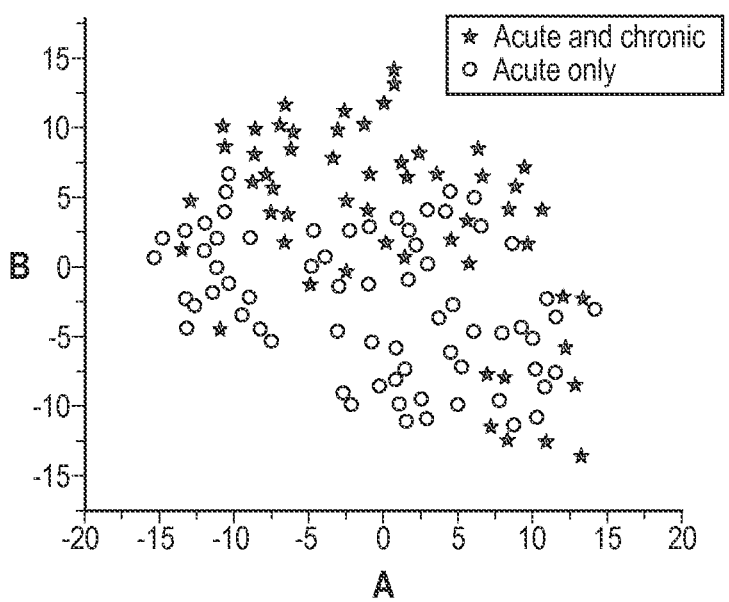
Figure 4C:
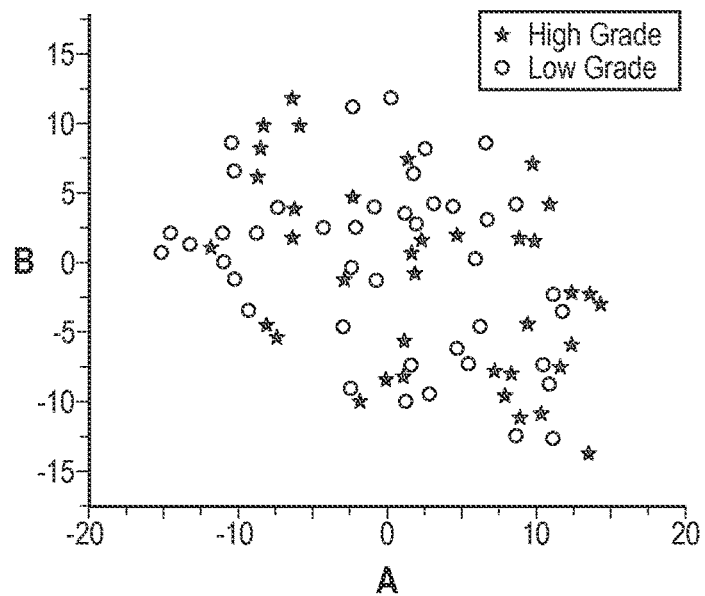
Figure 4D:
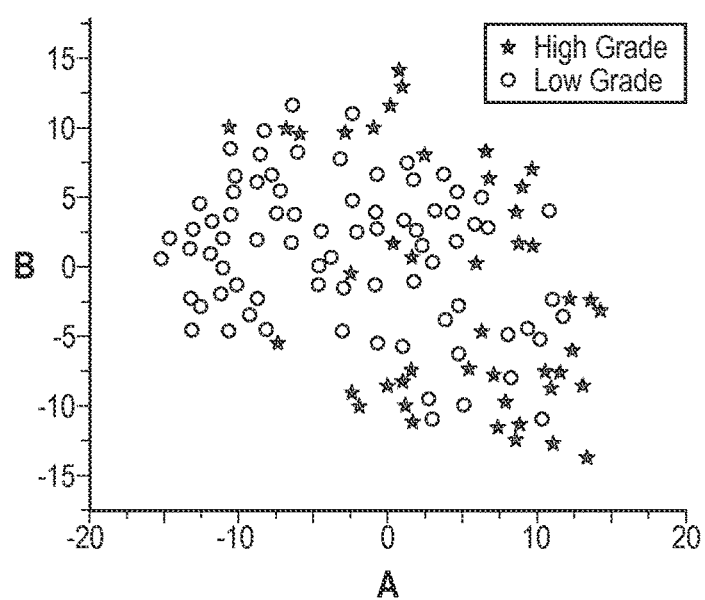
Figure 4E:
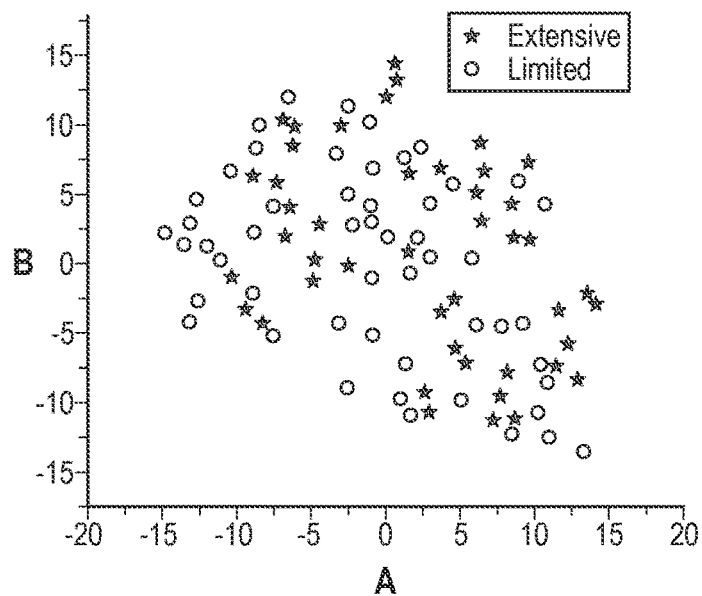
Figure 4F:
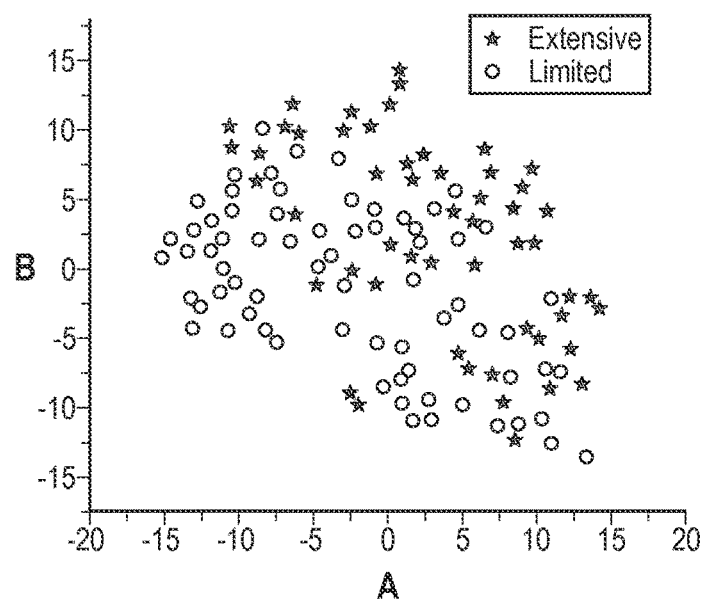
Figure 4I:
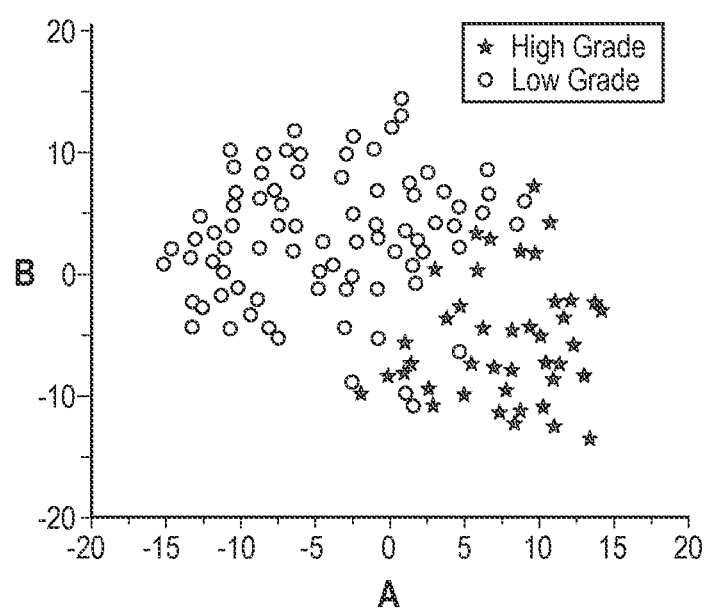

The partial clustering and interspersed nature of the two classes in plots of FIGS. 4B, 4D, and 4F illustrate the limited level of performance achieved by each individual classifier. In contrast, the plot of FIG. 4I allows the visualization of the clear separation between classes found by the semi-unsupervised approach.

CONCLUSIONS

We were able to create classifiers that were able to make some predictions on the four clinical questions we set out to address. The MMV performance of the classifiers is not spectacular and is best for the questions of extensive vs. limited cGvHD and for the detection of aGvHD overall, with overall accuracies of around 67%, while the best performance for the other questions does not exceed 60%. The best performance was achieved for the prediction of aGvHD, which is probably to be expected, as this is the event closest to the time point of sample collection (assuming this is post-transplant but before onset of any GvHD).

The ROC curves (FIG. 3) show that improved performance is possible for some of the clinical questions addressed by using a cutoff in the average probabilities rather than the modified majority vote results. In particular, it seems that, sensitivities/specificities of 63%/70% or 73%/65% for the question of cGvHD after aGvHD and 79%/65% for occurrence of aGvHD are achievable.

We will now explain how and why the sensitivity/specificity as demonstrated in the ROC curves could be adjusted. Clinical considerations should drive the choice of cutoffs for each of the four clinical questions we considered. Each ROC plot (FIG. 3) is generated from one CMC/D run or classifier generation exercise using FIG. 1. Instead of using our majority vote (or modified majority vote) idea, we calculate for each sample, the average probability produced from the logistic regression across all the realizations where that sample is in the test set (instead of the majority classification with 0.5 cutoff on the probability across all the realizations where that sample is in the test set, as we do for MMV). So, for each sample we get a number between 0 and 1, which corresponds to the average probability that the sample is assigned to one of the two classifications (whichever one we call Class 1). We can set a cutoff of 'p' (for any $0<=p<=1$), and put all samples that have an average probability below p in Class 2 and all samples that have an average probability above or equal to p in Class 1. As we increase p from 0 up to 1, we get sets of possible classifications for all the samples and the accuracy of these classifications is what we plot (in terms of the sensitivity and specificity of each set of classifications for each p) as the ROC curve. So, the ROC curve really shows results for a very large number of possible individual classifiers, which are parameterized by the cutoff, p. If we pick p=0.5, we usually get classifications, and resulting sensitivity and specificity, close to our MMV approach. However, we could pick any value of p, depending on where on our ROC curve gives us the most clinically useful test (sometimes one needs a very high sensitivity and sometimes a high specificity is better).

In principle, in reporting a panel of class labels, one for each clinical question, we could just return the 4 average probabilities, and not use any cutoffs at all. However, this raises issues with validation. To validate one would have to bin the results to some extent and as the number of bins increases, the number of samples needed to validate the results also increases, probably much faster. Hence it may be clinically preferable to return a panel of 4 binary labels, rather than four average probabilities.

The semi-unsupervised approach yielded a classification that retained some rather weak correlations with severity of aGvHD, but tests of association with the available clinical data did not show a clear association with the available clinical data. It is of interest to study whether the groups defined by this molecular characteristic have any relation with any other clinical characteristics or outcomes.

It is envisaged that in practice, classifiers described above for each of the 4 clinical questions would be used on a given sample and the report that would be provided to a clinician would take the form of a panel of class labels, one for each classifier.

Laboratory Test Center and Computer Configured as Classifier

FIG. 5 is an illustration of a laboratory testing center or system for processing a test sample (in this example a blood-based sample from a PHSC or bone marrow transplant patient) using a classifier generated in accordance with FIG. 1. The system includes a mass spectrometer 506 and a general purpose computer 510 having CPU 512 implementing a CMC/D classifier 520 coded as machine-readable instructions and a reference mass spectral data set including a feature table 522 of class-labeled mass spectrometry data stored in memory 514. It will be appreciated that the mass spectrometer 506 and computer 510 of FIG. 5 could be used to generate the CMC/D classifier 520 in accordance with the process of FIG. 1.

The operation of the system of FIG. 5 will be described in the context of a predictive test for occurrence or characterization of GvHD as explained above. The following discussion assumes that the CMC/D classifier 520 (and preferably multiple classifiers for multiple clinical questions relating to occurrence or characterization of GvHD) is already generated at the time of use of the classifier to generate a label or panel of labels for a test sample.

The system of FIG. 5 obtains a multitude of samples 500, e.g., blood-based samples (serum or plasma) from diverse patients receiving PHSC or bone marrow and generates a label or panel of labels as a fee-for-service. The samples 500 are used by the classifier (implemented in the computer 510) to make predictions as to whether the patient providing the sample is likely to develop aGvHD, cGvHD after aGvHD, predict the level or grade of aGvHD, or answer some other clinical question. The outcome of the test is a binary class label (or panel of such labels), such as Low Risk, Low or the like, or High Risk, High, or the like. The particular moniker for the class label is not particularly important and could be generic such as "class 1", "class 2" or the like, but as noted earlier the class label is associated with some clinical attribute relevant to the question being answered by the classifier.

The samples may be obtained on serum cards or the like in which the blood-based sample is blotted onto a cellulose or other type card. Aliquots of the sample are spotted onto several spots of a MALDI-ToF sample "plate" 502 and the plate inserted into a MALDI-ToF mass spectrometer 506. The mass spectrometer 506 acquires mass spectra 508 from each of the spots of the sample. The mass spectra are represented in digital form and supplied to a programmed general purpose computer 510. The computer 510 includes a central processing unit 512 executing programmed instructions. The memory 514 stores the data representing the mass spectra 508. Preferably, spectra from at least 100,000 laser shots are acquired, such as for example 800 shot spectra from 50 or more locations on a MALDI plate spot, repeated for three MALDI plate spots, and then averaged. See the above discussion of acquisition of spectra for use in generating the classifier; the same spectral acquisition methodology is used in generating a test result for a specimen after the classifier has already been created.

The memory 514 also stores a final CMC/D classifier 520, which includes a) a reference mass spectral data set 522 in the form of a feature table of N class-labeled spectra, where N is some integer number, in this example a development set used to develop the classifier as explained above or some sub-set of the development sample set. The final CMC/D classifier includes b) code 524 representing a KNN classification algorithm (which is implemented in the mini-classifiers as explained above), c) program code 526 for executing the final classifier generated in accordance with FIG. 1 on the mass spectra of patients, including logistic regression weights and data representing master classifier(s) forming the final classifier, and d) a data structure 528 for storing classification results, including a final class label (or panel of final class labels) for the test sample. The memory 514 also stores program code 530 for implementing the processing shown at 550, including code (not shown) for acquiring the mass spectral data from the mass spectrometer in step 552; a pre-processing routine 532 for implementing the background subtraction, normalization and alignment step 554 (details explained above), filtering and averaging of the 800 shot spectra at multiple locations per spot and over multiple MALDI spots to make a single 100,000+ shot average spectrum (as explained above) a module (not shown) for calculating integrated intensity values at predefined m/z positions in the background subtracted, normalized and aligned spectrum (step 556), and a code routine 538 for implementing the final classifier 520 using the reference dataset 522 on the values obtained at step 556. The process 558 produces a class label at step 560. The module 540 reports the class label(s) as indicated at 560 (i.e., "low", "high" or the equivalent). As explained previously, the classifier 520 may be replicated so as to constitute different classifiers for different clinical questions, each one using the same feature table 522, and KNN classification algorithm 524.

The program code 530 can include additional and optional modules, for example a feature correction function code 536 (described in co-pending U.S. patent application Ser. No. 14/486,442) for correcting fluctuations in performance of the mass spectrometer, a set of routines for processing the spectrum from a reference sample to define a feature correction function, a module storing feature dependent noise characteristics and generating noisy feature value realizations and classifying such noisy feature value realizations, modules storing statistical algorithms for obtaining statistical data on the performance of the classifier on the noisy feature value realizations, or modules to combine class labels defined from multiple individual replicate testing of a sample to produce a single class label for that sample. Still other optional software modules could be included as will be apparent to persons skilled in the art.

The system of FIG. 5 can be implemented as a laboratory test processing center obtaining a multitude of patient samples from oncologists, patients, clinics, etc., and generating a class label for the patient samples as a fee-for-service. The mass spectrometer 506 need not be physically located at the laboratory test center but rather the computer 510 could obtain the data representing the mass spectra of the test sample over a computer network.

FURTHER CONSIDERATIONS

It will be noted that the classifier we generated uses the features of Appendix A and we have not determined precisely what proteins these peaks correspond to. Nor is it necessary. What matters is classifier performance. We believe that they involve, directly or indirectly, common proteins involved in immune response, and likely may be one or more of the protein biomarkers mentioned in the scientific literature cited at the beginning of this document. Note that, with our "deep MALDI" mass spectrometry and the use of 50, 100 or even 200 or more peaks, it is likely that our classifiers are based on still undiscovered protein biomarkers circulating in serum. Our method essentially takes advantage of the fact that we can detect these proteins, and in particular low abundance proteins, using the >100,000 shot MALDI-TOF mass spectra, and use them in development and application of a classifier, even though we do not know precisely what proteins the peaks correspond to.

The following claims are offered as further description of the disclosed inventions.

APPENDIX A

Feature Definitions

| Left m/z | Center m/z | Right m/z |
|---|---|---|
| 3032.70 | 3042.84 | 3052.98 |
| 3076.36 | 3087.75 | 3099.13 |
| 3100.53 | 3110.30 | 3120.08 |
| 3123.35 | 3131.59 | 3139.84 |
| 3148.86 | 3158.61 | 3168.36 |
| 3192.06 | 3211.63 | 3231.21 |
| 3232.21 | 3243.81 | 3255.41 |
| 3255.61 | 3267.07 | 3278.54 |
| 3301.87 | 3321.97 | 3342.06 |
| 3356.08 | 3370.30 | 3384.52 |
| 3385.17 | 3397.57 | 3409.96 |
| 3410.47 | 3417.91 | 3425.35 |

APPENDIX A-continued

Feature Definitions

| Left m/z | Center m/z | Right m/z |
|---|---|---|
| 3425.56 | 3431.21 | 3436.86 |
| 3437.43 | 3447.65 | 3457.86 |
| 3458.17 | 3468.16 | 3478.14 |
| 3499.81 | 3511.07 | 3522.32 |
| 3542.23 | 3558.18 | 3574.13 |
| 3670.79 | 3684.56 | 3698.32 |
| 3698.48 | 3708.12 | 3717.77 |
| 3748.68 | 3758.55 | 3768.43 |
| 3768.49 | 3779.32 | 3790.16 |
| 3790.37 | 3799.68 | 3808.99 |
| 3809.25 | 3822.47 | 3835.69 |
| 3835.76 | 3845.41 | 3855.07 |
| 3887.10 | 3895.05 | 3903.00 |
| 3903.06 | 3910.23 | 3917.40 |
| 3917.57 | 3930.91 | 3944.25 |
| 3946.84 | 3957.24 | 3967.65 |
| 4002.96 | 4016.02 | 4029.08 |
| 4030.04 | 4038.01 | 4045.97 |
| 4046.27 | 4056.48 | 4066.68 |
| 4096.72 | 4104.47 | 4112.22 |
| 4131.37 | 4137.89 | 4144.41 |
| 4226.09 | 4232.96 | 4239.84 |
| 4241.65 | 4251.24 | 4260.84 |
| 4261.36 | 4270.69 | 4280.02 |
| 4280.35 | 4293.18 | 4306.02 |
| 4333.83 | 4344.16 | 4354.50 |
| 4354.70 | 4364.49 | 4374.27 |
| 4374.92 | 4388.57 | 4402.21 |
| 4402.41 | 4416.31 | 4430.22 |
| 4452.06 | 4460.52 | 4468.98 |
| 4469.11 | 4478.25 | 4487.39 |
| 4542.68 | 4551.03 | 4559.37 |
| 4559.55 | 4572.65 | 4585.74 |
| 4586.05 | 4591.16 | 4596.27 |
| 4596.37 | 4606.46 | 4616.54 |
| 4619.08 | 4639.33 | 4659.58 |
| 4672.29 | 4680.59 | 4688.88 |
| 4701.59 | 4718.55 | 4735.50 |
| 4750.65 | 4759.90 | 4769.16 |
| 4771.03 | 4789.51 | 4808.00 |
| 4808.67 | 4823.61 | 4838.54 |
| 4846.94 | 4860.25 | 4873.55 |
| 4880.39 | 4894.55 | 4908.71 |
| 4932.51 | 4943.32 | 4954.13 |
| 4955.12 | 4967.41 | 4979.70 |
| 4980.01 | 4988.88 | 4997.74 |
| 4998.05 | 5007.60 | 5017.14 |
| 5017.40 | 5029.71 | 5042.03 |
| 5042.19 | 5049.29 | 5056.39 |
| 5056.65 | 5072.94 | 5089.22 |
| 5095.81 | 5110.48 | 5125.16 |
| 5125.47 | 5137.37 | 5149.27 |
| 5224.98 | 5245.28 | 5265.59 |
| 5270.76 | 5293.34 | 5315.93 |
| 5357.56 | 5376.70 | 5395.84 |
| 5399.59 | 5413.52 | 5427.44 |
| 5427.85 | 5436.81 | 5445.77 |
| 5445.88 | 5457.27 | 5468.66 |
| 5468.97 | 5479.05 | 5489.12 |
| 5489.43 | 5499.86 | 5510.29 |
| 5514.14 | 5526.24 | 5538.35 |
| 5541.28 | 5562.81 | 5584.33 |
| 5673.66 | 5683.49 | 5693.31 |
| 5696.05 | 5712.91 | 5729.77 |
| 5730.18 | 5739.50 | 5748.81 |
| 5749.22 | 5772.11 | 5795.00 |
| 5795.51 | 5806.29 | 5817.08 |
| 5817.89 | 5827.71 | 5837.54 |
| 5837.74 | 5847.16 | 5856.58 |
| 5856.88 | 5868.33 | 5879.77 |
| 5886.25 | 5896.13 | 5906.00 |
| 5906.31 | 5916.54 | 5926.77 |
| 5981.76 | 5992.86 | 6003.95 |
| 6004.45 | 6014.83 | 6025.22 |
| 6025.52 | 6036.20 | 6046.89 |
| 6102.09 | 6115.41 | 6128.73 |

APPENDIX A-continued

Feature Definitions

| Left m/z | Center m/z | Right m/z |
|---|---|---|
| 6188.99 | 6202.21 | 6215.42 |
| 6280.65 | 6296.96 | 6313.26 |
| 6318.13 | 6335.39 | 6352.66 |
| 6390.34 | 6423.66 | 6456.98 |
| 6457.09 | 6466.25 | 6475.42 |
| 6475.72 | 6486.26 | 6496.79 |
| 6497.09 | 6505.80 | 6514.51 |
| 6515.63 | 6535.48 | 6555.33 |
| 6580.96 | 6593.11 | 6605.26 |
| 6605.57 | 6630.08 | 6654.59 |
| 6654.69 | 6664.62 | 6674.54 |
| 6674.84 | 6685.02 | 6695.20 |
| 6695.41 | 6706.04 | 6716.67 |
| 6717.08 | 6736.98 | 6756.88 |
| 6757.39 | 6767.01 | 6776.63 |
| 6790.00 | 6799.93 | 6809.86 |
| 6826.57 | 6841.61 | 6856.65 |
| 6856.75 | 6865.81 | 6874.88 |
| 6875.08 | 6896.81 | 6918.53 |
| 6919.54 | 6927.50 | 6935.45 |
| 6935.65 | 6952.77 | 6969.88 |
| 6970.08 | 6978.09 | 6986.09 |
| 6986.71 | 7003.52 | 7020.34 |
| 7030.97 | 7068.18 | 7105.40 |
| 7123.20 | 7151.27 | 7179.33 |
| 7180.82 | 7196.02 | 7211.23 |
| 7239.55 | 7265.03 | 7290.51 |
| 7290.66 | 7308.78 | 7326.90 |
| 7351.43 | 7365.36 | 7379.29 |
| 7379.47 | 7395.02 | 7410.58 |
| 7410.74 | 7425.53 | 7440.32 |
| 7440.88 | 7452.43 | 7463.98 |
| 7467.70 | 7482.61 | 7497.52 |
| 7502.95 | 7515.79 | 7528.63 |
| 7639.80 | 7675.45 | 7711.11 |
| 7734.60 | 7747.04 | 7759.48 |
| 7761.42 | 7786.06 | 7810.69 |
| 7813.93 | 7833.82 | 7853.71 |
| 8187.14 | 8207.39 | 8227.64 |
| 8228.13 | 8237.92 | 8247.70 |
| 8248.69 | 8272.96 | 8297.23 |
| 8353.20 | 8368.12 | 8383.05 |
| 8383.42 | 8395.43 | 8407.44 |
| 8407.56 | 8429.11 | 8450.66 |
| 8469.60 | 8484.71 | 8499.82 |
| 8500.07 | 8512.51 | 8524.96 |
| 8525.70 | 8539.51 | 8553.31 |
| 8559.26 | 8570.40 | 8581.55 |
| 8581.67 | 8594.30 | 8606.93 |
| 8623.77 | 8637.52 | 8651.26 |
| 8655.35 | 8665.20 | 8675.04 |
| 8676.40 | 8698.20 | 8719.99 |
| 8748.35 | 8769.65 | 8790.95 |
| 8803.21 | 8818.00 | 8832.80 |
| 8832.92 | 8843.51 | 8854.10 |
| 8865.62 | 8878.49 | 8891.37 |
| 8901.16 | 8921.15 | 8941.15 |
| 8941.28 | 8951.62 | 8961.96 |
| 8997.00 | 9006.78 | 9016.57 |
| 9017.19 | 9027.84 | 9038.48 |
| 9038.98 | 9048.52 | 9058.05 |
| 9059.16 | 9077.93 | 9096.69 |
| 9098.30 | 9153.59 | 9208.88 |
| 9272.77 | 9289.37 | 9305.96 |
| 9311.41 | 9323.23 | 9335.06 |
| 9335.68 | 9357.47 | 9379.27 |
| 9379.64 | 9389.48 | 9399.33 |
| 9402.05 | 9441.49 | 9480.93 |
| 9481.43 | 9495.98 | 9510.53 |
| 9553.99 | 9576.90 | 9599.81 |
| 9620.37 | 9645.57 | 9670.77 |
| 9670.89 | 9682.78 | 9694.67 |
| 9696.52 | 9722.71 | 9748.91 |
| 9785.31 | 9798.44 | 9811.56 |
| 9836.83 | 9870.38 | 9903.94 |
| 9906.67 | 9941.52 | 9976.38 |
| 10127.58 | 10155.38 | 10183.18 |
| 10201.14 | 10215.93 | 10230.73 |
| 10232.71 | 10242.62 | 10252.53 |
| 10252.77 | 10268.01 | 10283.24 |
| 10283.61 | 10291.84 | 10300.08 |
| 10300.20 | 10313.58 | 10326.95 |
| 10330.66 | 10349.30 | 10367.94 |
| 10434.19 | 10455.49 | 10476.79 |
| 10526.57 | 10542.73 | 10558.89 |
| 10567.31 | 10590.52 | 10613.74 |
| 10614.73 | 10639.00 | 10663.28 |
| 10704.88 | 10735.22 | 10765.56 |
| 10767.79 | 10784.75 | 10801.72 |
| 10815.59 | 10850.63 | 10885.68 |
| 10913.41 | 10930.63 | 10947.84 |
| 11029.88 | 11059.83 | 11089.78 |
| 11094.73 | 11114.39 | 11134.05 |
| 11135.75 | 11157.66 | 11179.56 |
| 11427.79 | 11445.33 | 11462.86 |
| 11464.20 | 11481.45 | 11498.69 |
| 11502.47 | 11540.26 | 11578.05 |
| 11610.17 | 11630.48 | 11650.79 |
| 11654.57 | 11689.29 | 11724.01 |
| 11724.79 | 11739.31 | 11753.82 |
| 11755.03 | 11765.43 | 11775.83 |
| 11776.31 | 11794.09 | 11811.86 |
| 11872.81 | 11909.45 | 11946.09 |
| 12275.75 | 12301.26 | 12326.78 |
| 12423.28 | 12461.61 | 12499.95 |
| 12531.63 | 12567.55 | 12603.46 |
| 12603.95 | 12623.78 | 12643.61 |
| 12657.88 | 12677.47 | 12697.06 |
| 12721.97 | 12743.86 | 12765.75 |
| 12765.99 | 12785.95 | 12805.90 |
| 12808.80 | 12870.96 | 12933.12 |
| 12935.29 | 12973.99 | 13012.69 |
| 13033.49 | 13076.54 | 13119.59 |
| 13121.28 | 13138.33 | 13155.38 |
| 13155.63 | 13169.53 | 13183.44 |
| 13266.40 | 13283.45 | 13300.50 |
| 13308.24 | 13328.55 | 13348.87 |
| 13349.35 | 13369.55 | 13389.74 |
| 13553.72 | 13574.65 | 13595.57 |
| 13596.53 | 13616.37 | 13636.20 |
| 13699.56 | 13723.63 | 13747.69 |
| 13747.94 | 13789.29 | 13830.65 |
| 13832.59 | 13849.76 | 13866.93 |
| 13867.17 | 13902.36 | 13937.55 |
| 13937.79 | 13951.94 | 13966.09 |
| 13966.33 | 13989.67 | 14013.01 |
| 14015.19 | 14042.64 | 14070.09 |
| 14084.84 | 14103.71 | 14122.57 |
| 14136.84 | 14161.88 | 14186.91 |
| 14187.39 | 14210.73 | 14234.07 |
| 14235.04 | 14262.01 | 14288.97 |
| 14290.91 | 14311.95 | 14332.99 |
| 14459.24 | 14488.26 | 14517.29 |
| 14518.25 | 14545.22 | 14572.19 |
| 14573.16 | 14602.06 | 14630.96 |
| 14753.58 | 14791.67 | 14829.77 |
| 16912.41 | 16939.37 | 16966.34 |
| 17008.67 | 17035.88 | 17063.08 |
| 17110.00 | 17131.41 | 17152.81 |
| 17153.30 | 17169.26 | 17185.22 |
| 17228.52 | 17272.29 | 17316.07 |
| 17356.94 | 17405.31 | 17453.68 |
| 17453.93 | 17480.89 | 17507.86 |
| 17574.61 | 17613.43 | 17652.25 |
| 18241.90 | 18285.07 | 18328.24 |
| 18562.34 | 18633.21 | 18704.07 |
| 20877.65 | 20945.25 | 21012.85 |
| 21013.33 | 21073.68 | 21134.02 |
| 21134.50 | 21183.36 | 21232.21 |
| 21232.94 | 21283.12 | 21333.31 |

APPENDIX A-continued

Feature Definitions

| Left m/z | Center m/z | Right m/z |
|---|---|---|
| 21669.49 | 21707.59 | 21745.68 |
| 21745.92 | 21768.90 | 21791.87 |
| 22973.59 | 23044.82 | 23116.05 |

We claim:

1. A method for assessing a risk of a patient receiving a transplant of pluripotent hematopoietic stem cells (PHSC) or bone marrow developing graft-versus-host disease or characterizing such disease, comprising the steps of:
    (a) performing MALDI-TOF mass spectrometry on a blood-based sample obtained from the patient after the PHSC or bone marrow transplant by subjecting the sample to at least 100,000 laser shots and acquiring mass spectral data;
    (b) obtaining integrated intensity values in the mass spectral data of a multitude of pre-determined mass-spectral features; and
    (c) operating on the mass spectral data with a programmed computer implementing a classifier configured as a combination of filtered mini-classifiers using a regularized combination method,
    wherein in the operating step the classifier compares the integrated intensity values with feature values of a training set of class-labeled mass spectral data obtained from a multitude of patients having received a transplant of PHSC or bone marrow with the values obtained in step (b) with a classification algorithm and generates a class label for the sample, wherein the class label is associated with the risk of a patient providing the sample developing graft-versus-host disease or characterizing the graft-versus-host disease.

2. The method of claim 1, wherein the operating step is performed multiple times by different classifiers, each configured as a combination of filtered mini-classifiers using a regularized combination method and addressing a different clinical question associated with the development or characterization of graft-versus-host disease, and the method further comprising the step of generating a panel of class label results, one for each operating step.

3. The method of claim 2, wherein one of the classifiers addresses the clinical question of whether the patient is likely to develop acute graft-versus host disease.

4. The method of claim 2, wherein one of the classifiers addresses the clinical question of whether the patient is likely to develop acute graft-versus host disease at grade II or higher as compared to not developing acute-graft-versus-host disease or developing acute graft-versus-host disease only at grade 1.

5. The method of claim 2, wherein one of the classifiers addresses the clinical question of whether the patient is likely to develop chronic graft-versus-host disease after developing acute graft-versus-host disease.

6. The method of claim 1, wherein the obtaining step (b) comprises obtaining integrated intensity values of at least 50 features listed in Appendix A.

7. The method of claim 6, wherein the obtaining step comprises obtaining integrated intensity values of at least 100 features listed in Appendix A.

8. The method of claim 6, wherein the obtaining step comprises obtaining integrated intensity values of at least 200 features listed in Appendix A.

9. A classifier for assessing a risk of a patient receiving a transplant of pluripotent hematopoietic stem cells (PHSC) or bone marrow developing graft-versus-host disease or characterizing such disease, comprising in combination:
    a memory storing a reference set of mass spectral data obtained from blood-based samples from a multitude of patients having received a transplant of PHSC or bone marrow and an associated class label;
    a programmed computer configured to implement a classifier configured as a combination of filtered mini-classifiers with drop-out regularization;
    wherein the reference set of mass spectral data includes feature values of at least some of the m/z features listed in Appendix A.

10. The classifier of claim 9, wherein the reference set of mass spectral data is obtained from each of the blood-based samples by applying at least 100,000 laser shots to the blood-based samples using MALDI-TOF mass spectrometry.

11. A laboratory testing system for conducting tests on blood-based samples from patients receiving pluripotent hematopoietic stem cells (PHSC) or bone marrow transplants and assessing risk of the patients developing graft-versus-host disease or characterizing such disease, comprising:
    a MALDI-TOF mass spectrometer configured to conduct mass spectrometry on a blood-based sample from a patient by subjecting the sample to at least 100,000 laser shots and acquiring resulting mass spectral data;
    a memory storing a reference set of mass spectral data obtained from a multitude of patients having received a transplant of PHSC or bone marrow and associated class label; and
    a programmed computer configured to implement a classifier configured as a combination of filtered mini-classifiers with drop-out regularization;
    wherein the reference set of mass spectral data includes feature values of at least some of the m/z features listed in Appendix A;
    wherein the programmed computer is programmed to generate a class label for the sample, wherein the class label is associated with a risk of a patient providing the sample developing graft-versus-host disease or characterizing such disease.

* * * * *